US005811261A

United States Patent [19]
Wallach et al.

[11] Patent Number: 5,811,261
[45] Date of Patent: Sep. 22, 1998

[54] EXPRESSION OF THE RECOMBINANT TUMOR NECROSIS FACTOR BINDING PROTEIN I (TBP-I)

[75] Inventors: David Wallach, Rehovot; Yaron Nophar, Ramat Gan, both of Israel; Oliver Kemper, Bockenheim, Germany; Hartmut Engelmann, Munich, Germany; Cord Brakebusch, Braunschweig, Germany; Dan Aderka, Holon, Israel

[73] Assignee: Yeda Research and Development Co. Ltd., Rehovot, Israel

[21] Appl. No.: 126,016

[22] Filed: Sep. 24, 1993

Related U.S. Application Data

[63] Continuation of Ser. No. 625,668, Dec. 13, 1990, abandoned, which is a continuation-in-part of Ser. No. 243,092, Sep. 12, 1988, abandoned.

[30] Foreign Application Priority Data

Dec. 13, 1989 [IL] Israel .......................................... 92697
Jul. 12, 1990 [IL] Israel .......................................... 95064

[51] Int. Cl.$^6$ ...................................................... C12P 21/06
[52] U.S. Cl. .................... 435/69.1; 435/70.1; 435/320.1; 435/325; 435/358; 435/366; 530/350
[58] Field of Search ................................. 435/69.1, 70.1, 435/172.3, 240.2, 320.1, 325, 358, 366; 424/85.1; 530/350, 351; 930/144

[56] References Cited

FOREIGN PATENT DOCUMENTS

| 5897690 | 7/1990 | Australia . |
| 0393438 | 10/1990 | European Pat. Off. . |
| 0417563 | 3/1991 | European Pat. Off. . |
| 2218101 | 3/1989 | United Kingdom . |

OTHER PUBLICATIONS

Livneh et al, J.Biol.Chem. 261:12490–12497, 1986.
Old, L.J., "Tumor Necrosis Factor," *Sci. Am.–258*, pp. 41–49.
Beutler, B. et al.. "Purification of Cachectin, A Lipoprotein Lipase–Suppressing Hormone Secreted by Entotoxin–Induced Raw 264.7 Cells," *J. Exp. Med. 161*, pp. 984–995.
Espevik, T. et al., "Characterization of Binding and Biological Effects of Monoclonal Antibodies Against A Human Tumor Necrosis Factor Receptor," (1990) *J. Exp. Med. 171*, pp. 415–426.
Engelmann, H. et al., "A Tumor Necrosis Factor–binding Protein Purified to Homogeneity from Human Urine Protects Cells from Tumor Necrosis Factor Toxicity," (1989) *J. Biol. Chem. 264*, pp. 11974–11980.

Engelmann, H. et al., "Two Tumor Necrosis Factor–binding Proteins Purified from Human Urine," (1990) *J. Biol. Chem. 265*, pp. 1531–1536.
Olsson, I. et al., "Isolation and Characterization of a Tumor Necrosis Factor Binding Protein from Urine," (1989) *Eur. J. Haematol. 42*, pp. 270–275.
Seckinger, P. et al., "Purification and Biologic Characterization of a Specific Tumor Necrosis Factor Inhibitor," (1989a) *J. Biol. Chem 264*, pp. 11966–11973.
Mosley, B. et al., "The Murine Interleukin–4 Receptor: Molecular Cloning and Characterization of Secreted and Membrane Bound Forms," (1989) *Cell 59*, pp. 335–348.
Goodwin, R.G. et al., "Cloning of the Human and Murine Interleukin–7 Receptors: Demonstration of a Soluble Form and Homology to a New Receptor Superfamily," (1990) *Cell 60*, pp., 941–951.
Loetscher, H. et al., "Molecular Cloning and Expression of the Human 55 kd Tumor Necrosis Factor Receptor," (1990), *Cell 61*, pp. 351–359.
Schall, T. et al., "Molecular Cloning and Expression of a Receptor for Human Tumor Necrosis Factor," (1990) *Cell 61*, pp. 361–370.
Binkert, C. et al., (1989) *The EMBO Journal*, vol. 8, No. 9, pp. 2497–2502. "Cloning, sequence analysis and expression of a cDNA encoding a novel insulin–like growth factor binding protein (IGFBP–2)."
Gatanaga, T. et al., (1990) *PNAS USA*, vol. 87, pp. 8781–8784. "Purification and characterization of an inhibitor (soluble tumor necrosis factor receptor) for tumor necrosis factor and lymphotoxin obtained from the serum ultrafiltrates of human cancer patients."
Heller, R.A. et al., (1990) *Journal of Biological Chemistry*, vol. 265, No. 10, pp. 5708–5717. "Amplified Expression of Tumor Necrosis Factor Receptor in Cells Transfected with Epstein–Barr Virus Shuttle Vector cDNA Libraries."
Peetre, C. et al., (1988) *European Journal of Haematology*, vol. 41, No. 5, pp. 414–419. "A tumor necrosis factor binding protein is present in human biological fluids."

Primary Examiner—Stephen Walsh
Assistant Examiner—Eliane Lazar-Wesley
Attorney, Agent, or Firm—Browdy and Neimark

[57] ABSTRACT

Tumor Necrosis Factor Binding Protein I (TBP-I), precursors and analogs thereof, are produced by transfecting eukaryotic cells with an expression vector comprising al DNA molecule encoding the whole human type I TNF receptor or a soluble domain thereof, and culturing the transfected cells, whereby the soluble proteins are secreted into the medium.

7 Claims, 13 Drawing Sheets

FIG. 1A
a    Asp Ser Val Cys Pro Gln Gly Lys Tyr Ile His Pro Gln
b
```
         GGI GTC CCI TTC ATA TAA GTA GGI GT
          T       T       G   G   G
                                      T
```
c
```
         GGA GTC CCA TTC ATA TA
          C       T   C   T   G
          T           G
          G           T
```
d
```
                     TTC ATA TAA GTA GGA GT
                         T   G   G   G   C
                                 T   G
                                     T
```
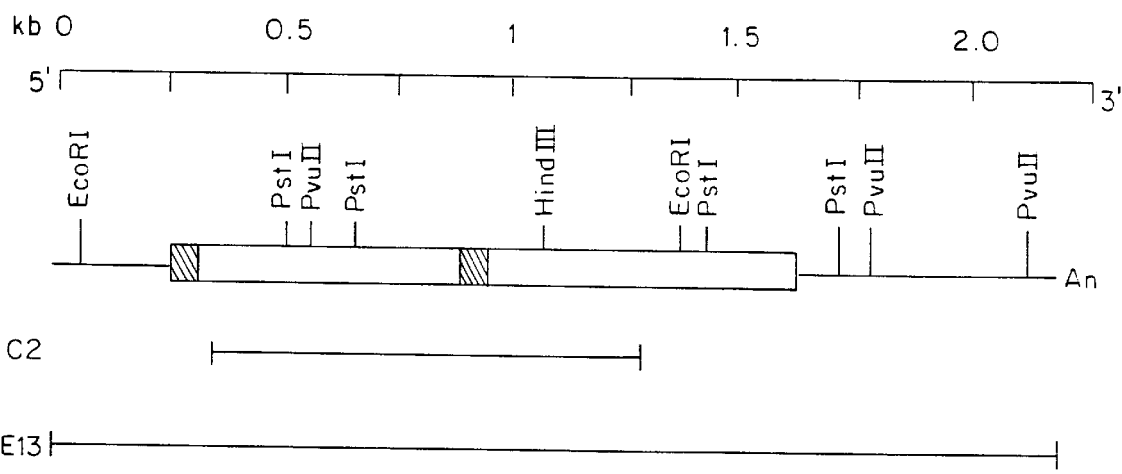
FIG. 1B
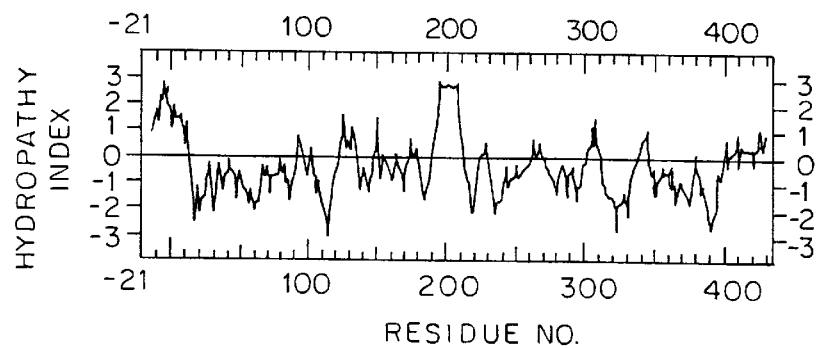
FIG. 1C

FIG.1D(1)

```
  1                                                                         CGGCCCAGTGATCTTGA   17
 18  ACCCCAAAGGCCACAACTGGAGCCTCAGTCCAGAGAATTCTGAGAAAATTAAAGCAGAGGAGGGAGAGATCACTGGGA  136
137  CTGTCACCCCAAGGCACTTGGGACGTCCTGGACAGACCCGAGTCCTGCCGAGCCCCAGCACTGCCCTCCCACACTGCCCTGAGCCCAAATGGGGAGTGAGAGCCATAGCTGTCTGGC  255
                      -21                                                                                      -10
                      Met Gly Leu Ser Thr Val Pro Asp Leu Leu Leu Gln Leu Leu Val Gly
                                                                                    -1  +1
256  ATG GGC CTC TCC ACC GTG CCT GAC CTG CTG CTG CAG CTG CTG GTG GGA ATA TAC CCC TCA GGG GTT ATT GGA CTG  345
                                                                                        Ile Tyr Pro Ser Gly Val Ile Gly Leu
      *
               10                                   20                                    30
     Val Pro His Leu Gly Asp Arg Glu Lys Arg Asp Ser Val Pro Gln Gly Lys Tyr Ile His Pro Gln Asn Asn Ser Ile Cys Cys Thr
346  GTC CCT CAC CTA GGG GAC AGG GAG AAG AGA GAT AGT GTG CCC CAA GGA AAA TAT ATC CAC CCT CAA AAT AAT TCG ATT TGG TGT ACC  435
                         40                                    50                                    60
     Lys His Lys Gly Thr Tyr Leu Tyr Asn Asp Cys Pro Gly Pro Gly Gln Asp Thr Asp Arg Glu Cys Glu Ser Gly Ser Phe Thr
436  AAG TGC CAC AAA GGA ACC TAC TTG TAC AAT GAC TGT CCA GGC CCG GGG CAG GAT ACG GAC AGG GAG TGC GAG AGC GGC TCC TTC ACC  525
                         70                                    80                                    90
     Ala Ser Glu Asn His Leu Arg His Cys Leu Ser Cys Lys Ser Lys Cys Arg Lys Glu Met Gly Gln Val Glu Ile Ser Cys Thr Val Asp
526  GCT TCA GAA AAC CAC CTC AGA CAC TGC CTC AGC TGC AAA TCA AAA TGC CGA AAG GAA ATG GGT CAG GTG GAG ATC TCT TCT TGC ACA GTG GAC  615
```

FIG. 1D(2)

```
                                  100                                                  110                                                  120
            Arg Asp Thr Val Cys Gly Cys Arg Lys Asn Gln Tyr Arg His Tyr Trp Ser Glu Asn Leu Phe Gln Cys Phe Asn Cys Ser Leu Cys Leu
 616        CGG GAC ACC GTG TGT GGC TGC AGG AAG AAC CAG TAC CGG CAT TAT TGG AGT GAA AAC CTT TTC CAG TGC TTC AAT TGC AGC CTC TGC CTC    705
                       130                                                  140                                                  150
            Asn Gly Thr Val His Leu Ser Cys Gln Glu Lys Gln Asn Thr Val Cys His Ala Gly Phe Phe Leu Arg Glu Asn Glu Cys Val
 706        AAT GGG ACC GTG CAC CTC TCC TGC CAG GAG AAA CAG AAC ACC GTG TGC CAT GCA GGT TTC TTT CTA AGA GAA AAC GAG TGT GTC         795
                       160                                                  170                                                  180
            Ser Cys Ser Asn Cys Lys Lys Ser Leu Glu Cys Thr Lys Leu Cys Leu Pro Gln Ile Glu Asn Val Lys Gly Thr Glu Asp Ser Gly Thr
 796        TCC TGT AGT AAC TGT AAG AAG AGC CTG CAG ACG TGC AAG TTG TGC CTA CCC CAG ATT GAG AAT GTT AAG GGC ACT GAG GAC TCA GGC ACC    885
                       190                                                  200                                                  210
            Thr Val Leu Pro Leu Val Ile Phe Phe Phe Gly Leu Cys Leu Leu Ser Leu Leu Phe Ile Gly Leu Met Tyr Arg Tyr Gln Arg Trp Lys
 886        ACA GTG CTG TTG CCC CTG GTC ATT TTC TTT TTT GGT CTT TGC CTT CTC TTA TCC CTC TTC ATT GGT TTA ATG TAT CGC TAC CAA CGG TGG AAG    975
                       220                                                  230                                                  240
            Ser Lys Leu Tyr Ser Ile Val Cys Gly Lys Ser Pro Thr Lys Pro Glu Lys Gly Glu Leu Glu Gly Thr Thr Thr Lys Pro Leu Ala Pro Asn
 976        TCC AAG CTC TAC TCC ATT GTT TGT GGG AAA TCG ACA CCT AAA CAG GAG CTT GAA GGA ACT ACT ACT AAG CCC CTG GCC CCA AAC         1065
                       250                                                  260                                                  270
            Pro Ser Phe Ser Pro Thr Pro Gly Phe Thr Pro Thr Leu Gly Phe Ser Pro Val Pro Ser Ser Thr Phe Thr Ser Ser Ser Thr Tyr Thr
1066        CCA AGC TTC AGT CCC ACT CCC GGC TTC ACC CCT ACC CTG GGC TTC AGT CCC GTG CCC AGT TCC ACC TTC ACC TCC AGC TCC TCC ACC TAT ACC    1155
```

FIG. 1D(3)

```
                                                                                           300
           280                       290
      Pro Gly Asp Cys Pro Asn Phe Ala Ala Pro Arg Arg Glu Val Ala Pro Pro Tyr Gln Gly Ala Asp Pro Ile Leu Ala Thr Ala Leu Ala
1156  CCC GGT GAC TGT CCC AAC TTT GCG GCT CCC AGA GAG GTG GCA CCA CCC TAT CAG GGG GCT GAC CCC ATC CTT GCG ACA GCC CTC GCC  1245
           310                       320                       330
      Ser Asp Pro Ile Pro Asn Pro Leu Gln Lys Trp Glu Asp Ser Ala His Lys Pro Gln Ser Leu Asp Thr Asp Asp Pro Ala Thr Leu Tyr
1246  TCC GAC CCC ATC CCC AAC CCC CTT CAG AAG TGG GAG GAC AGC GCC CAC AAG CCA CAG AGC CTA GAC ACT GAT GAC CCC GCG ACG CTG TAC  1335
           340                       350                       360
      Ala Val Val Glu Asn Val Pro Pro Leu Arg Trp Lys Glu Phe Val Arg Arg Leu Gly Leu Ser Asp His Glu Ile Asp Arg Leu Glu Leu
1336  GCC GTG GTG GAG AAC GTG CCC CCG TTG CGC TGG AAG GAA TTC GTG CGG CGG CTA GGG CTG AGC GAC CAC GAG ATC GAT CGG CTG GAG CTG  1425
           370                       380                       390
      Gln Asn Gly Arg Cys Leu Arg Glu Ala Gln Tyr Ser Met Leu Ala Thr Trp Arg Arg Thr Pro Arg Glu Ala Thr Leu Glu Leu
1426  CAG AAC GGG CGC TGC CTG CGC GAG GCG CAA TAC AGC ATG CTG GCC ACC TGG AGG CGG CCC ACG CGG CGC GAG GCC ACG CTG GAG CTG  1515
           400                       410                       420
      Leu Gly Arg Val Leu Arg Asp Met Asp Leu Leu Gly Cys Leu Glu Asp Ile Glu Glu Ala Leu Cys Gly Pro Ala Ala Leu Pro Pro Ala
1516  CTG GGA CGC GTG CTC CGC GAC ATG GAC CTG CTG GGC TGC CTG GAG GAC ATC GAG GAG GCG CTT TGC GGC CCC GCC GCC CTC CCG CCC GCG  1605
           430
      Pro Ser Leu Leu Arg End
1606  CCC AGT CTT CTC AGA TGA  GGCTGCGCCCTGCGGGCAGCTCTAAGGACCGTCCTGCGAGATCGCCTTCCAACCCCACTTTTTCTGGAAAGGAGGGTCCTGCAGGGCAAGCA  1718
                              *
1719  GGAGCTAGCAGCCGCCTACTTGGTGCTAACCCCTCGATGTACATAGCTTTTCTCAGCTGCTGCTGCGCGCCGACAGTCAGCGCTGTGCCGCCGTGTGCGCGCCGAGAGAGTGCCGCCTCAAG  1837
1838  AGCCTGAGTGGGTTTGCGAGGATGAGGAGACGCTATGCCTCATGCCGTTTGGGTGTCCTCACCAGCAAGGCTGCTCGGGGCCCCTGGTTCGTCCTGAGCCTTTTCACAGTGC  1956
1957  ATAAGCAGTTTTTTTGTTTTGTTTTTGTTTTTAAATCATGTTACACTATGTTAAATCAATCATGTTGTTTGTTTTGTTTTTAAATCATGTTACACTAATAGAACTGGCACTCCTGTGCCCTCTGCCACTCCTGTCCTCTGCCTCCTCTGACAAGCACATAGCAAGCTGAAC  2075
2076  TGTCCTAAGGCAGGGGCAGGGGCGACCACGGAACAATGGGCCTTCAGCTGAGCTGGACTTTTGTACATACACTAAAATTCTGAAGTTAAAAAAAAAAAAAA  2175
```

EXPRESSION OF THE RECOMBINANT TUMOR NECROSIS FACTOR BINDING PROTEIN I (TBP-I)

CROSS-REFERENCE TO RELATED APPLICATIONS

The present application is a continuation of application Ser. No. 07/625,668, filed Dec. 13, 1990, now abandoned, which was a continuation-in-part of application Ser. No. 07/243,092, filed Sep. 12, 1988, now abandoned.

FIELD OF THE INVENTION

The present invention relates to human Tumor Necrosis Factor (TNF) binding Protein I, herein designated TBP-I, and more particularly, to the cloning of thee gene coding for said protein and its expression in host cells.

BACKGROUND OF THE INVENTION

TNF-$\alpha$ and TNF-$\beta$ (lymphotoxin) are structurally related polypeptide cytokines, produced primarily by mononuclear leukocytes, whose effects on cell function constitute a major factor in the elicitation of the inflammatory response. The TNFs affect cells In different ways, some of which resemble the functional modes of other inflammatory mediators, like interleukin-1 (IL-1) and interleukin-6 (IL-6). What appears most distinctive regarding the activity of the TNFs is that many of their effects can result in cell and tissue destruction. Increasing evidence that over-induction of these destructive activities contributes to the pathogenesis of a number of diseases, makes it of particular interest to elucidate their mechanisms and the ways they are regulated (Old, L. J. (1988) Sci.Am. 258, pp. 41–49).

High affinity receptors, to which both TNF-$\alpha$ and TNF-$\alpha$ bind Beutler, B. A., et al. (1985) J.Exp.Med. 161, pp. 984–995) play a key role in the initiation and in the control of the cellular response to these cytokines. These receptors are expressed on the surfaces of a variety of different cells. Studies showing that antibodies reacting with their extracellular portions affect cell in a manner very similar to the TNFs demonstrate that the receptors and cellular components associated with them are sufficient to provide the intracellular signaling for the effects of the TNFs (Espevik, T., et al., (1990) J.Exp.Med. 171, pp. 415–426).

Other studies have shown that molecules related to the TNF receptors (TNF-Rs) exist also in soluble forms. Two immunologically distinct species of such soluble TNF-Rs, designates TNF Binding Proteins I and II, or TBP-I and TBP-II, respectively, were recently isolated from human urine (Engalmann, H., et al., (1989) J.Biol.Chem. 264, pp. 11974–11980; Engelmann, H., et al., (1990) J.Biol.Chem. 265, pp. 1531–1536; Oluson, I., et al. (1989) Eur.J.Haematol. 42, pp. 270–275; Seckinger, P., et al., (1989a) J.Biol.Chem. 264, pp 11966–11973). Immunological evidence indicated that the two proteins are structurally related to two molecular species of the call surface TNF-R (the type I and type II receptors, respectively). Antibodies to each of the two soluble proteins were shown to block specifically the binding of TNF to one of the two receptors and could be used to immunoprecipitate the receptors. Antibodies against one of the two soluble proteins (TBP-I) were also found to induce effects characteristic of TNF in cells which express the immunologically cross-reactive cell receptors (Engelmann, H., et al., (1990) ibid.). Like the cell surface receptors for TNF, the soluble forms of these receptors specifically bind TNF and can thus interfere with its binding to cells. It was suggested that they function as physiological inhibitors of TNF activity (Engelmann et al., 1989 (ibid.); Olseon et al., 1989 (ibid.); Seckinger et al., 1989a (ibid.)).

Soluble forms of cell surface receptors may be derived from the cell surface form of the receptor by proteolytic cleavage, or by a different mechanism proposed in two recent studies describing the cloning of the cDNAs for the receptors to IL-4 and IL-7. Besides cDNA clones encoding the full length receptors, clones which encode truncated, soluble forms of these receptors were also isolated in these studies. It was suggested that these latter clones are derived from transcripts specifically encoding soluble forms of the receptors, transcribed from the same genes which encode the cell surface forms, but differently spliced (Mosley, B., et al., (1989) Cell 59, pp. 335–348; Goodwin, R. G., at al., (1990) Cell 60, pp. 941–951).

Two recent studies have described the molecular cloning and expression of human type I TNF cell surface receptor (Loetacher, H., et al. (1990) Cell 61, pp. 351–359; Schall, T. J., et al., (1990) Cell 61, pp. 361–370).

SUMMARY OF THE INVENTION

The present invention relates to the production of human TBP-I, precursors and analogs thereof, by a method comprising transfection of eukaryotic, preferably CHO, cells with an expression vector comprising a DNA molecule encoding the whole type I human TNF receptor or a soluble domain thereof. When the whole DNA molecule is used, soluble proteins are produced by the transfected cells, along with the cell surface receptor, and are secreted into the medium.

The invention further relates to soluble proteins selected from precursors and analogs of TBP-I, which are secreted into the medium by eukaryotic cells transfected with a DNA molecule encoding the whole human type I TNF receptor or a soluble domain thereof.

DESCRIPTION OF THE DRAWINGS

FIG. 1 shows the nucleotide sequence of the type I TNF receptor cDNA and the predicted amino acid sequence of the encoded protein.

(A) shows the probes used for screening for the cDNA wherein:

(a) shows the $NH_2$-terminal amino acid sequence of TBP-I, SEQ ID NO:2, amino acids 20-32;

(b) shows synthetic oligonucleotide probes, SEQ ID NO:3, designed on the basis of the $NH_2$-terminal amino acid sequence, used for initial screening; and (c) and (d) are probes, SEQ ID NO:4 and SEQ ID NO:5, respectively, overlapping with (b), used to confirm the validity of clones isolated in the initial screening.

(B) is the schematic presentation of the cDNA clones isolated from a human colon (C2) and from CEM-lymphocytes (E13) libraries and a diagram of the complete cDNA structure. Untranslated sequences are represented by a line. Coding regions are boxed. The shaded portions represent the sequences which encode the signal peptide and the transmembrane domains.

(C) shows the hydropathy profile of the predicted amino acid sequence of the TNF receptor. Hydrophobicity (above the line) and hydrophilicity (below the line) values were determined using the sequence analysis software package of the University of Wisconsin genetic computer group (UWCG) according to Kyte and Doolittle (1982). The curve is the average of the hydrophobicity index for each residue over a window of nine residues.

(D) depicts the nucleotide (SEQ ID NO:1) and predicted amino acid sequences, SEQ ID NO:2, of the type I TNF receptor. The presumptive start and stop signals are denoted by asterisks; the three sequences derived from TBP-I by broken overlining; the transmembrane and leader domains by round-ended boxes; and the four repetitive sequences in the extracellular domain by thick underlining. Cysteine residues are boxed. Glycosylation sites are overlined and the presumptive polyadenylation signal is underlined.

Figure 2:
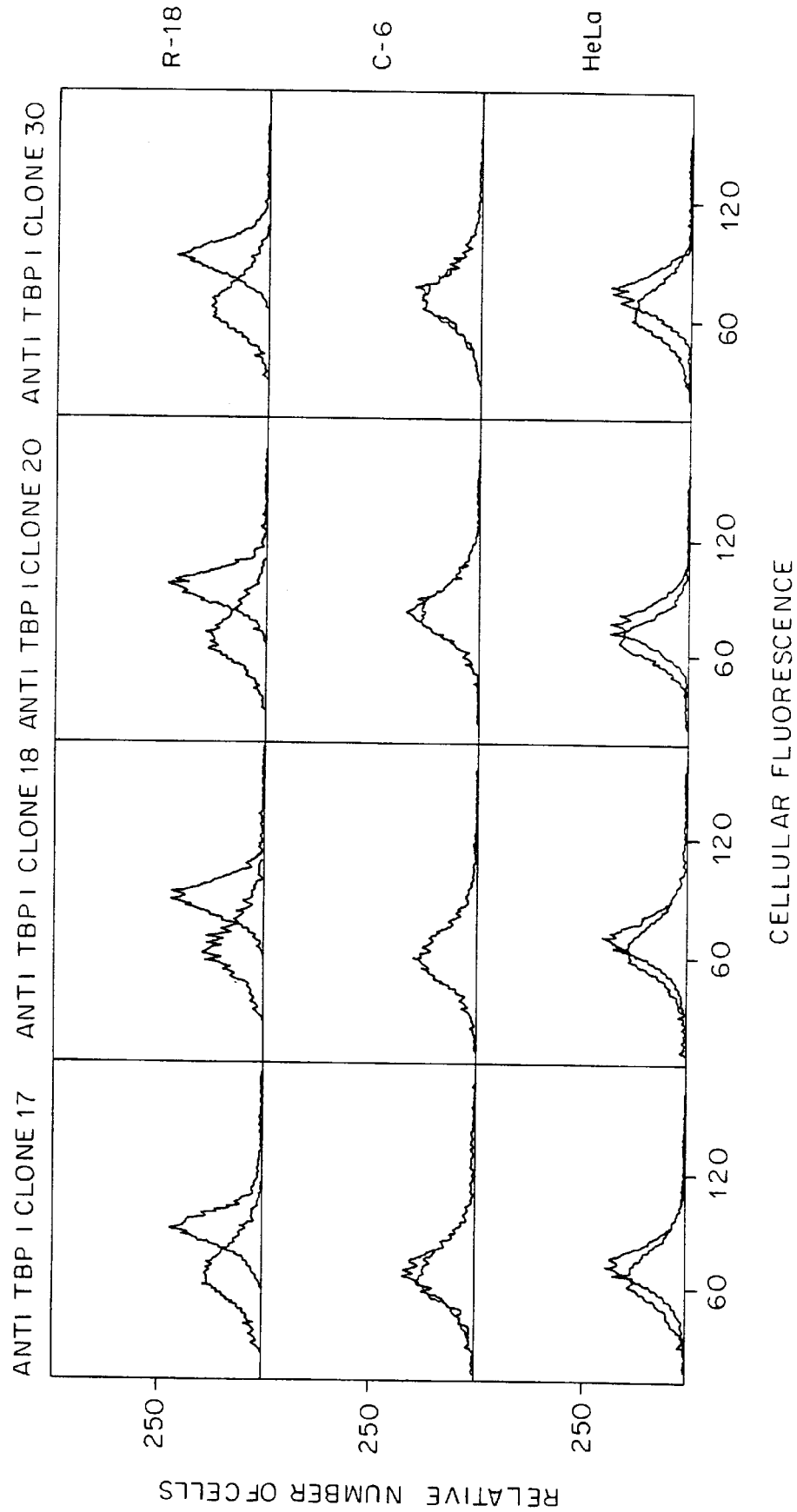

FIG. 2 shows the detection of type I TNF-R using monoclonal antibodies to TBP-I in CHO cells transfected with E13 cDNA.

CHO cells, clones R-18 (transfected with an expression vector in which the E13 cDNA was placed under the control of an SV40 promoter) and C-6 (control; a clone of cells transfected with an expression vector in which E13 was placed in the inverse orientation), and HeLa cells, were stained with the anti-TBP-I monoclonal antibodies 17, 18, 20 and 30 followed by incubation with FITC conjugated anti-mouse F(ab). Fluorescence intensity was compared with that observed when a mouse monoclonal antibody against TNF was used in the first step of the staining as a control.

Figure 3A:
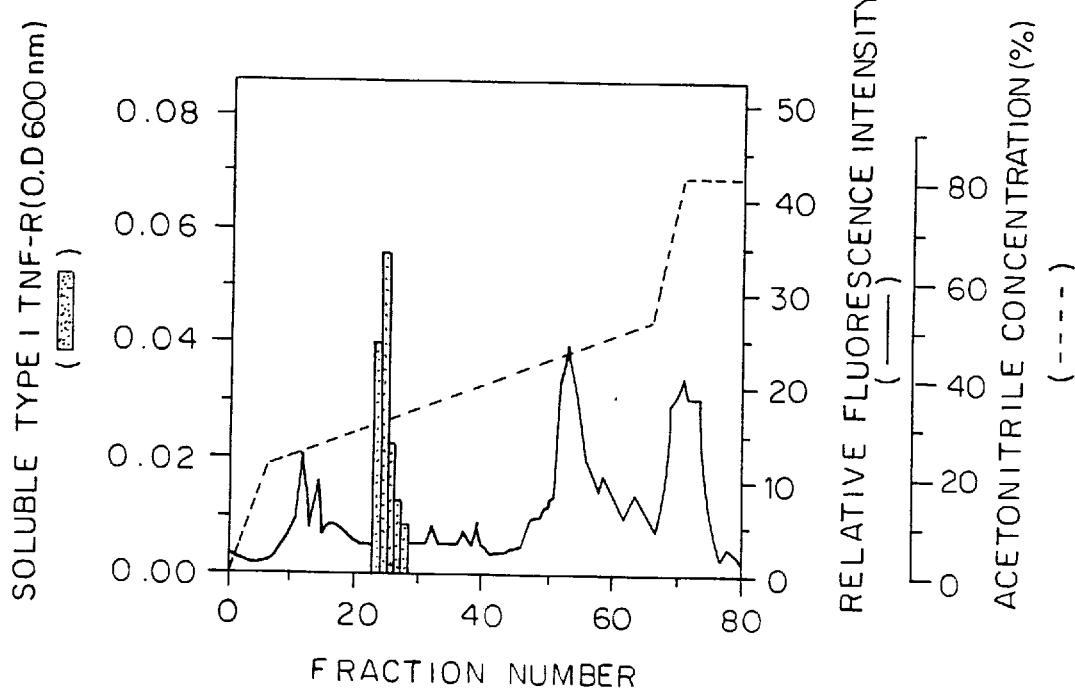
Figure 3B:
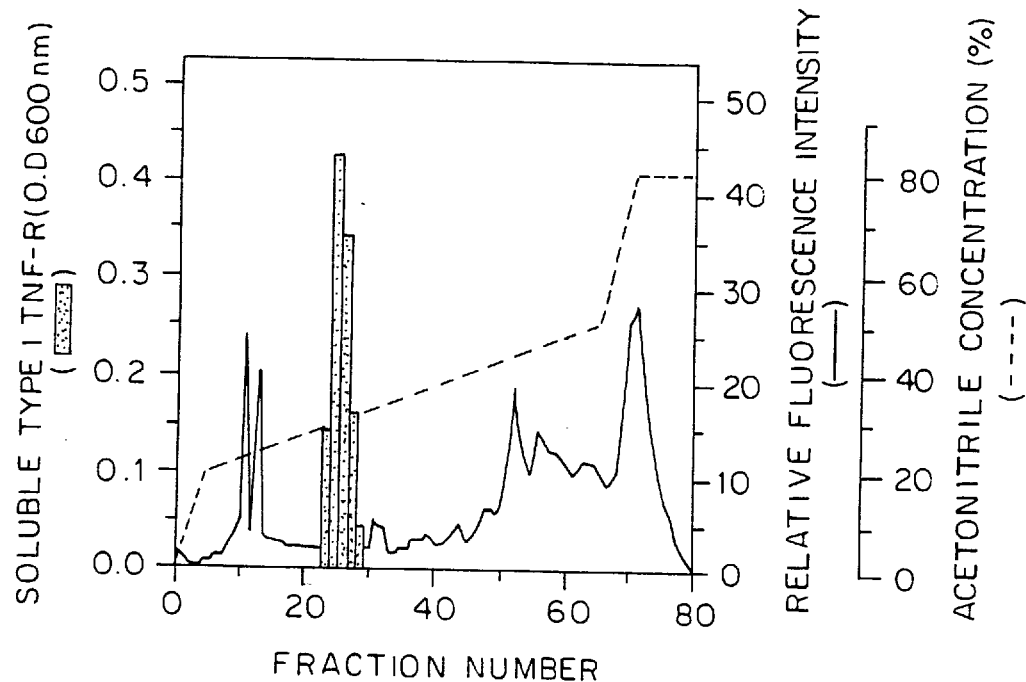

FIG. 3 shows reversed phase HPLC of the CHO-produced, soluble form of the type I TNF-R.

A concentrate of the conditioned medium of the CHO R-18 clones (see FIG. 2) and a concentrate of the CHO C-6 clone to which 3 ng pure TBP-I was added, were applied to an Aquapore RP300 column. Elution was performed with a gradient of acetonitrile in 0.3% aqueous trifluoroacetic acid (- - -), Fractions were examined for content of protein (—) and of the soluble form of the type I receptor by an ELISA (as described in Example 1; Procedures). None of the eluted fractions of a concentrate of the CHO C-6 clone, without addition of TBP-I, was found to contain any detectable amounts of the soluble form of the receptor (not shown).

Figure 4:
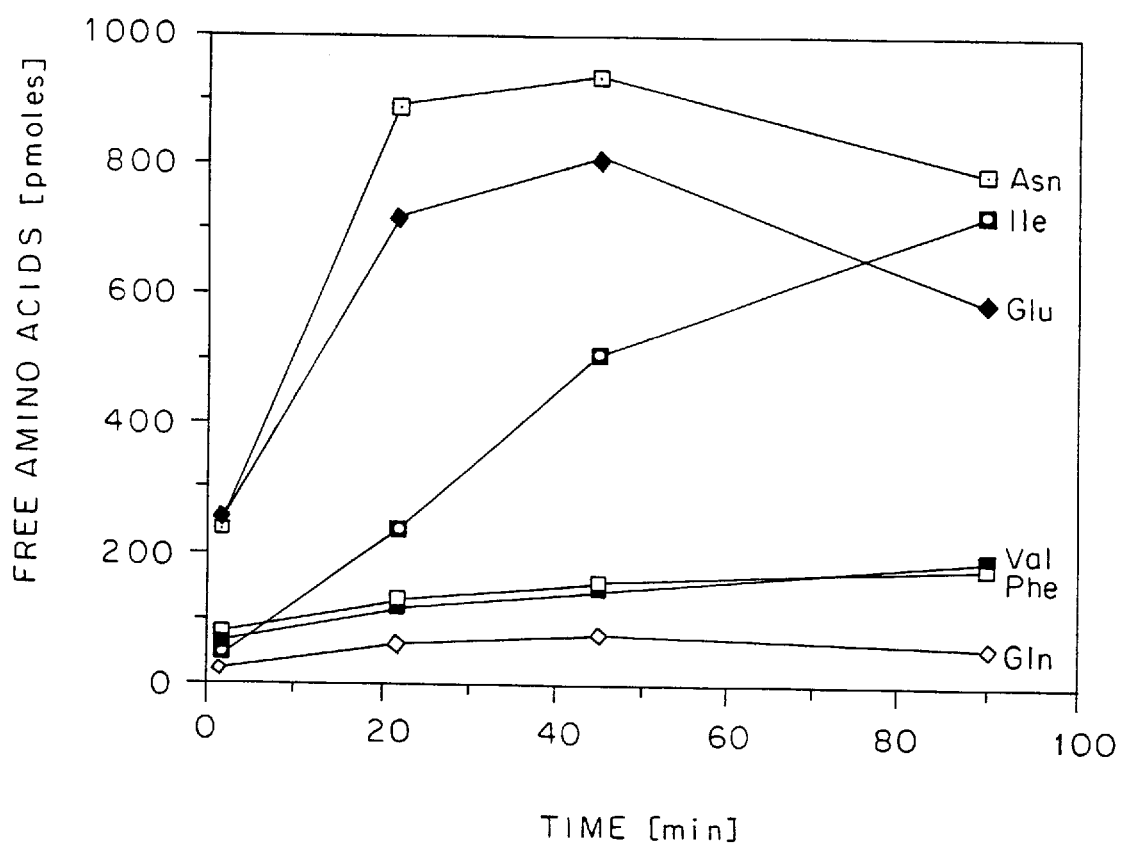

FIG. 4 shows the time course of the release of COOH-terminal amino acids from TSF-I by carboxypeptidase Y.

Figure 5A:
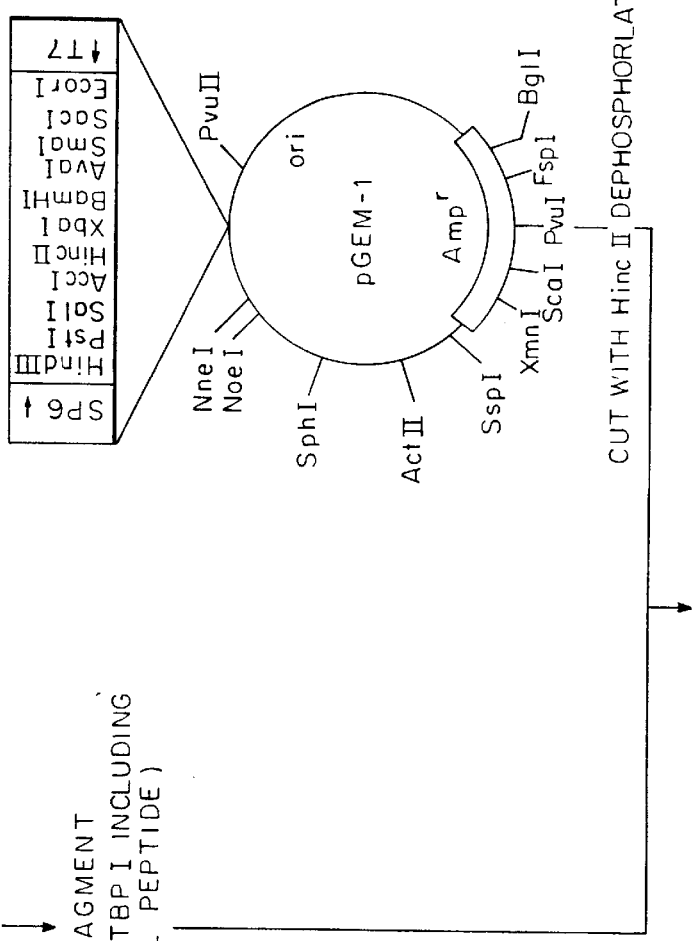
Figure 5B:
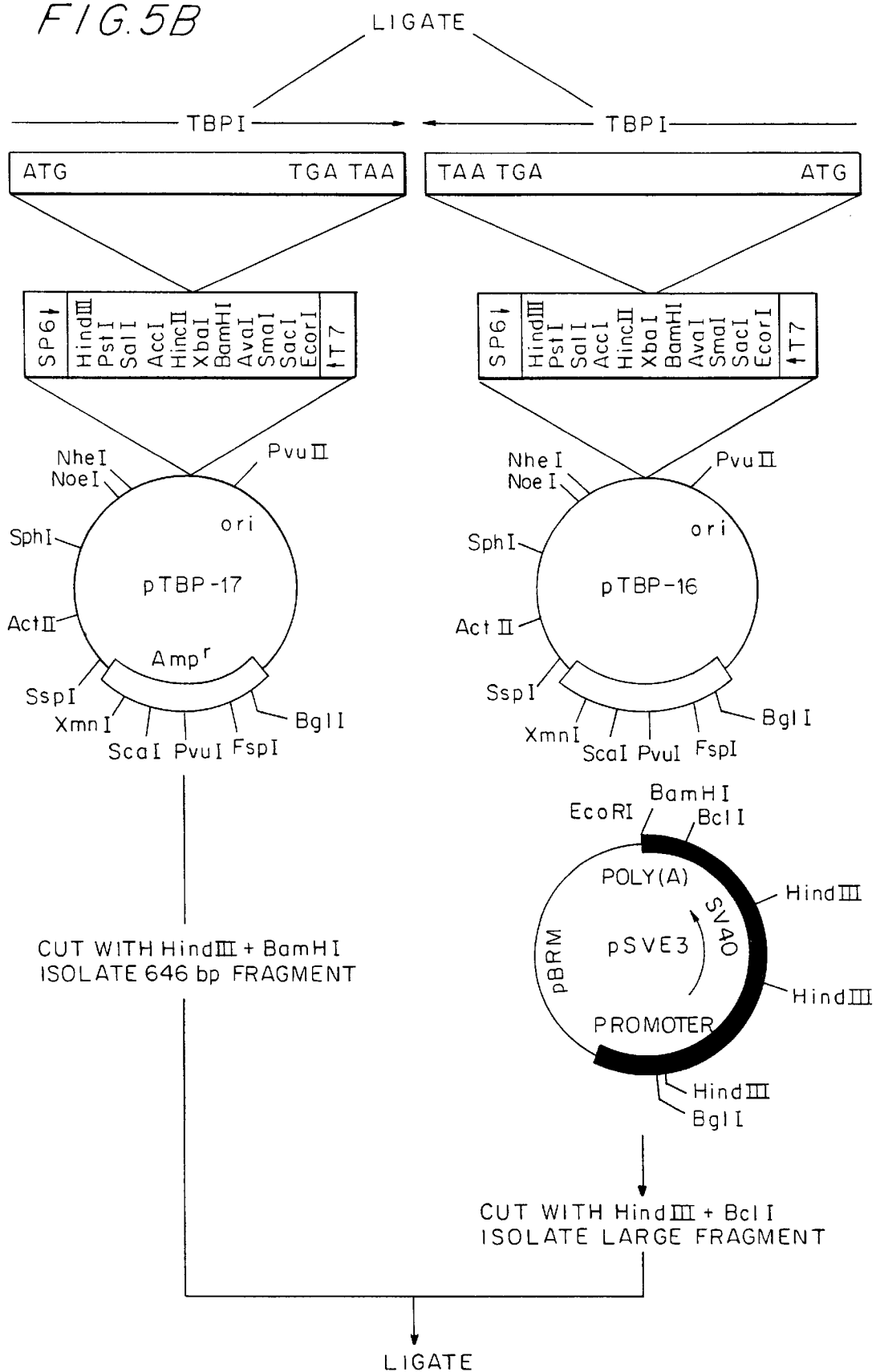
Figure 5C:
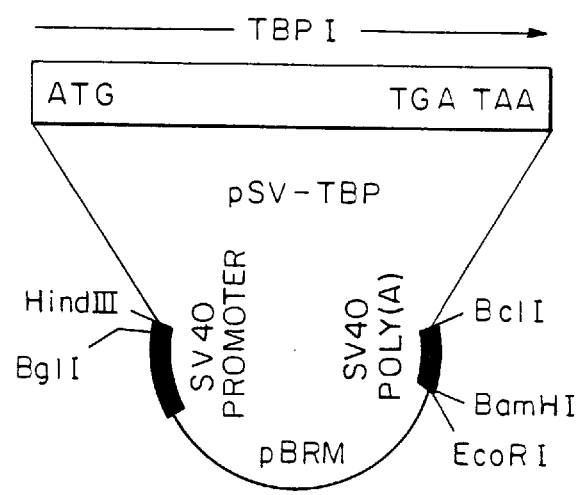

FIG. 5 shows the construction of plasmid pSV-TBP, which contains the DNA sequence encoding TBP-I fused to the strong SV40 early gene promoter. The construction starts with a DNA fragment coding for TBP-I including the signal peptide and extending to amino acid 180 (SEQ ID NO:1, nucleotides 256-858, nucleotides 256-276 and 836-856 being specifically shown). This was obtained by PCR amplification using the 5' primer (SEQ ID NO:6) and the 3' primer (SEQ ID NO:7) shown. Further details of the construction are set forth in Example 4.

Figure 6A:
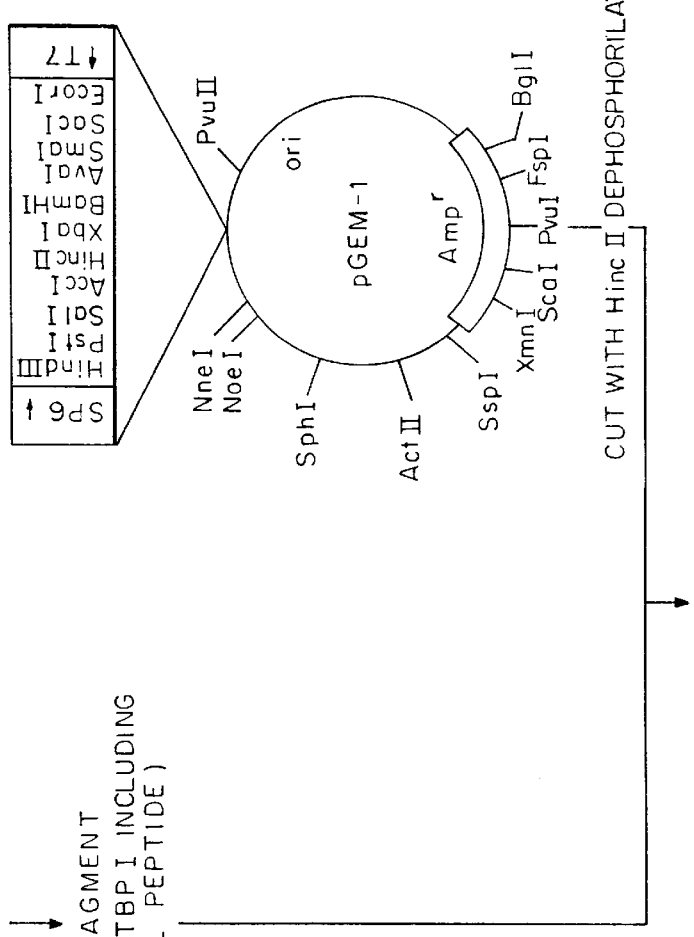
Figure 6B:
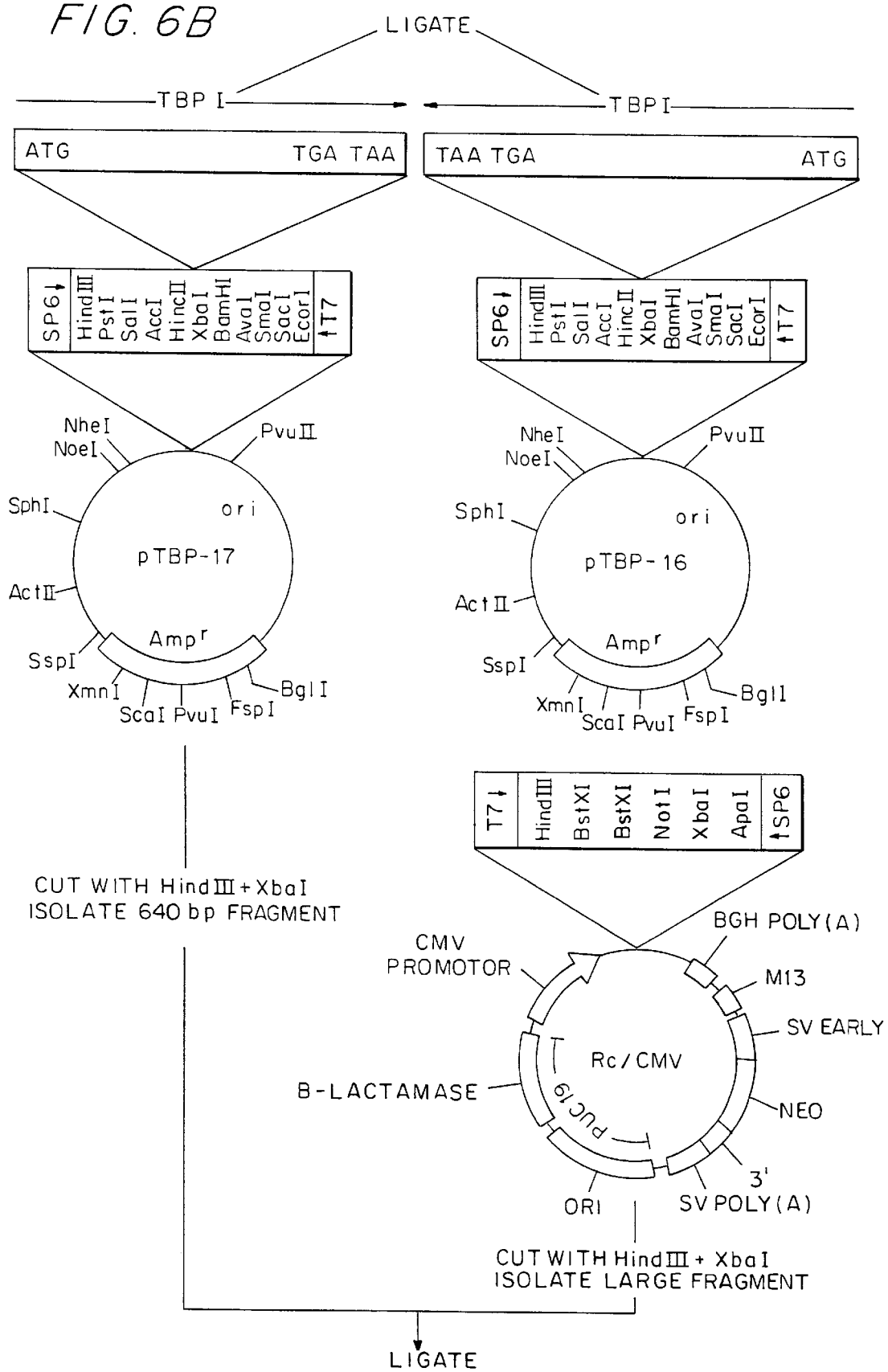
Figure 6C:
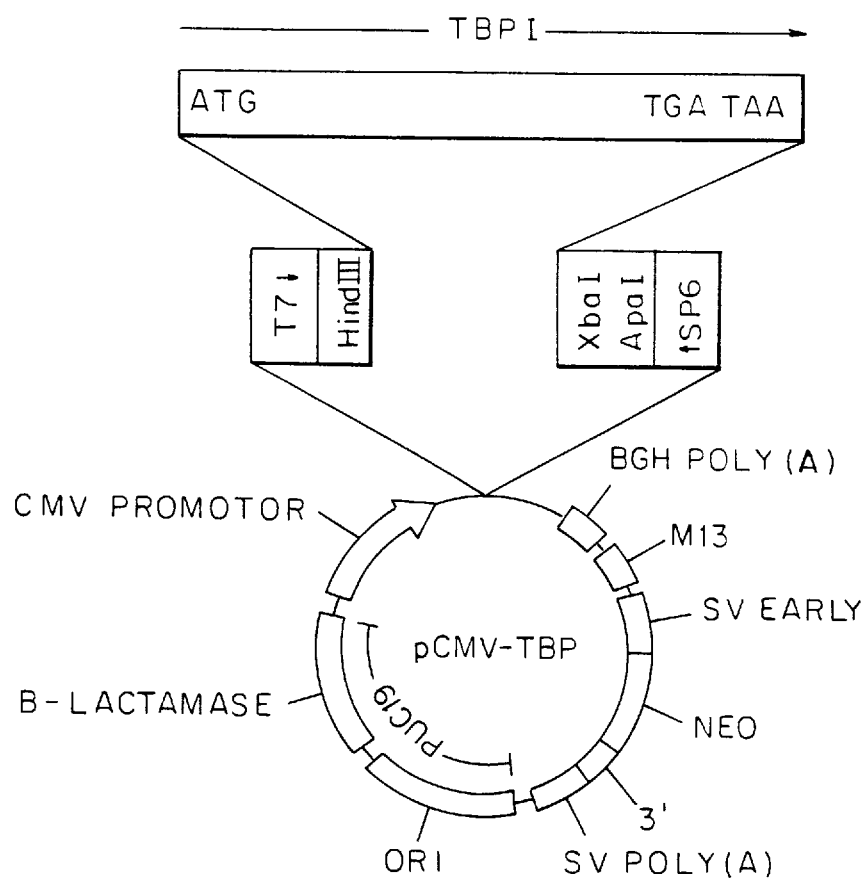

FIG. 6 shows the construction of the plasmid pCMV-TBF, which contains the DNA sequence encoding TBP-I fused to the cytomegalovirus (CMV) promoter. The TNF receptor DNA (SEQ ID NO:1, nucleotides 256-858) and the PCR primers (SEQ ID NO:6 and SEQ ID NO:7) used are the same as in the construction of FIG. 5.

DESCRIPTION OF THE INVENTION

Purified TBP-I isolated from human urine was described in U.S. Ser. No. 07/243,092 of the present applicants and shown to contain at the N-terminus the amino acid sequence shown in FIG. 1Aa.

The COOH-terminal of TBP-I was determined now and shown to contain a major fraction containing the sequence Ile-Glu-Asn denoted by broken overlining at positions 178-180 in FIG. 1D (SEQ ID NO:2), and at least one minor fraction including at least two further amino acids Val-Lys at positions 181-182.

The invention relates to a method for the production of a soluble recombinant protein selected from human Tumor Necrosis Factor Binding Protein I (TBP-I), biologically active precursors and analogs thereof, which comprises:

i) transfecting eukaryotic cells with an expression vector comprising a DNA molecule encoding the whole type I human TNF receptor or a soluble domain thereof, and ii) culturing the transfected cells, whereby the desired protein is produced and secreted into the medium.

The DNA sequence encoding the whole type I TNF receptor is depicted in FIG. 1D (SEQ ID NO:1). The soluble domain thereof includes the sequence down to position 180 (Asn) or 182 (Lys) or even some additional amino acids after position 182.

The soluble proteins produced by the transfected cells according to the method of the invention and secreted into the medium may have at the N-terminus the sequence Asp-Ser-Val denoted by broken overlining at positions 20-23 in FIG. 1D (TBP-I) (SEQ ID NO:2), or the sequence Leu-Val-Pro at positions 9-11 or Ile-Tyr-Pro at positions 1-3 or any other sequence between Ile(+1) and Asp(20). The proteins may have at the COOH terminal any of the sequences described above. All these soluble proteins, if biologically active with TBP-I-like activity, are encompassed by the invention as precursors and analogs of TBP-I.

According to the invention, oligonucleotide probes designed on the basis of the NH$_2$-terminal amino acid sequence of TBP-I, were synthesized by known methods and used for screening for the cDNA coding for TBP-I in cDNA libraries. In a human colon cDNA library, a C2 cDNA insert was found which hybridized to said probes and it was used for further screening in a human CEM-lymphocytes lambda ZAP cDNA library, thus leading to the cDNA shown in FIG. 1D (SEQ ID NO:1).

The DNAs of positive clones were then inserted into appropriately constructed expression vectors by techniques well known in the art. In order to be capable of expressing a desired protein, an expression vector should comprise also specific nucleotide sequences containing transcriptional and translational regulatory information linked to the DNA coding for the desired protein in such a way as to permit gene expression and production of the protein. The gene must be preceded by a promoter in order to be transcribed. There are a variety of such promoters in use, which work with different efficiencies (strong and weak promoters).

The DNA molecule comprising the nucleotide sequence coding for a protein comprising the amino acid sequence of TBP-I, i.e. TBP-I, a precursor or an analog thereof, preceded by a nucleotide sequence of a signal peptide and the operably linked transcriptional and translational regulatory signals is inserted into a vector which is capable of integrating the desired gene sequences into the host cell chromosome. The cells which have stably integrated the introduced DNA into their chromosomes can be selected by also introducing one or more markers which allow for selection of host cells which contain the expression vector.

In a preferred embodiment, the introduced DNA molecule will be incorporated into a plasmid or viral vector capable of autonomous replication in the recipient host. Factors of importance in selecting a particular plasmid or viral vector include the ease with which recipient cells that contain the vector may be recognized and selected from those recipient cells which do not contain the vector; the number of copies of the vector which are desired in a particular host and whether it is desirable to be able to "shuttle" the vector between host cells of different species. Once the vector or DNA sequence containing the construct(s) has been prepared for expression, the DNA construct(s) may be introduced into an appropriate host cell by any of a variety of suitable means: transformation, transfection, conjugation, protoplast fusion, electroporation, calcium phosphate precipitation, direct microinjection, etc.

Host cells to be used in this invention may be either prokaryotic or eukaryotic. Prokaryotic hosts, such as bacteria, e.g. *E.coli*, are used only when the cDNA encoding the soluble domain of the type I TNF receptor is used to transfect the cells. Under such conditions, the protein will not be glycosylated. The prokaryotic host must be compatible with the replicon and control sequences in the expression plasmid.

Eukaryotic cells are transfected according to the invention with plasmids comprising the cDNA encoding the whole type I TNF receptor. Preferred eukaryotic hosts are mammalian cells, e.g., human, monkey, mouse and chinese hamster ovary (CHO) cells. They provide the soluble form of the protein, besides the cell surface receptor, and provide post-translational modifications to protein molecules including correct folding or glycosylation at correct sites. The eukaryotic cells may also be transfected with a plasmid comprising a cDNA encoding a soluble domain of the human typo I TNF receptor molecule. Preferred mammalian cells according to the invention are CHO cells.

After the introduction of the vector, the host cells are grown in a selective medium, which selects for the growth of vector-containing cells. Expression of the cloned gene sequence(s) results in the production of the desired soluble protein, that is secreted into the medium, and may then be isolated and purified by any conventional procedure involving extraction, precipitation, chromatography, electrophoresis, or the like.

In a preferred embodiment, CHO cells are transfected with the type I TNF-R cDNA shown in FIG. 1D (SEQ ID NO:1) and they produce both the cell surface receptor and TBP-I, its soluble form, and/or precursors and analogs thereof.

The data presented in the present application are consistent with the notion that TBP-I—the soluble form for the type I TNF-R—constitutes a fragment of the cell surface form of this receptor, corresponding to its extracellular domain. The receptor is recognized by several monoclonal antibodies to TBP-I which interact with several spatially distinct epitopes in this protein. The amino acid sequence in the extracellular domain matches the sequence of TBP-I.

Particularly informative with regard to the mechanism of formation of TBP-I is the finding described in the present application, that a soluble form of the type I TNF-R is produced by CHO cells which were transfected with the TNF-R cDNA. This implies that cells possess some mechanism(s) which allow(s) the formation of the soluble form of the TNF-R from that same transcript that encodes the cell surface form.

The low rate of production of the soluble form of the type I TNF-R by the E13-transfected CHO cells does not necessarily reflect maximal activity. In HT29 cells, the spontaneous release of a soluble form of type I TNF-R occurs at about a 10-fold higher rate than that observed with the CHO-R-18 clone.

A likely mechanism whereby soluble forms of TNF receptors can be derived from the same transcripts which encode the cell surface forms is proteolytic cleavage. Indeed, flanking the amino acid residue which corresponds to the $NH_2$-terminus of TBP-I there are, within the sequence of amino acids of the receptor, two basic amino acid residues (Lys-Arg) which can serve as a site of cleavage by trypsin-like proteases. The identity of the proteases which might cause cleavage to take place at the COOH terminus of TBP-I is not known.

The invention will be illustrated by the following examples:

EXAMPLE 1

PROCEDURES

A) Determination of amino acid sequences within the TNF-binding proteins TBP-I and TBP-II The TNF Binding Proteins TBP-I and TBP-II were isolated from concentrated preparations of urinary proteins, as described previously (Engelmann, H., et al., (1990) J.Biol.Chem. 265, pp. 1531–1536) by ligand (TNF) affinity chromatography followed by reversed phase HPLC. TBP-I was cleaved with cyanogen bromide, yielding two peptides which, following reduction and alkylation, were isolated by reversed phase HPLC. The two peptides (CNBr-1 and CNBr-2 in Table I) were subjected to $NH_2$-terminal sequence analysis on a pulsed liquid gas phase protein microsequencer (Model 475A, Applied Biosystems Inc., Foster City Calif.). The sequence found for one of the peptides (CNBr-1) was identical to the $NH_2$ sequence of the intact TBP-I protein.

The COOH terminal sequence of amino acids in TBP-I was determined by digestion of the protein with carboxypeptidase Y followed by sequential analysis of the released amino acids. A sample of pure TBP-I (32 $\mu$g) was mixed with 1 nmole of norleucine, as an internal standard dried thoroughly and resuspended in 8 $\mu$l 0.1M sodium acetate buffer, pH 5.5, containing 0.8 $\mu$g carboxypeptidase Y (Sigma, St. Louis, Mo.). Digestion was performed at room temperature. 2 $\mu$l Aliquots withdrawn at various time points were acidified by adding 3 $\mu$l of 10% acetic acid to each, followed by addition of 15 $\mu$l 0.5% EDTA. They were then subjected to automated amino acid analysis (Applied Biosystems, U.K. model 420A). The results (shown in FIG. 4) indicate the sequence -Ile-Glu-Asn-COOH. Minor fractions were detected containing two or more additional amino acids.

Sequences within TBP-II were determined by generation of tryptic peptides of the protein. A sample of pure TBP-II (200 $\mu$g) was reduced, alkylated and repurified on an Aquapore RP-300 reversed-phase HPLC column. Fractions containing the modified protein were pooled and the pH was adjusted to 8.0 with $NaHCO_3$. Digestion with TPCK-trypsin (238 U/mg, Millipore Corp., Freehold, N.J.) was performed for 16 h. at room temperature at an enzyme to substrate ratio of 1:20 (w/w). The digest was loaded on a $C_1$ RP-P reversed phase HPLC column (Synchrom, Linden, Ind.) and the peptides separated by a linear 0 to 40% acetonitrile gradient in 0.3% aqueous trifluoroacetic acid. The $NH_2$ terminal amino acid sequences of the peptides and of the intact protein (N-terminus) are presented in Table I. The peptides were numbered according to their sequences of elution from the RP-P column. In the fractions denoted as 39,44,46,53 and 54, where heterogeneity of sequences was observed, both the major and the secondary sequences are presented.

b) Isolation of cDNA clones

Three mixtures of synthetic oligonucleotide probes (FIGS. 1Ab, 1Ac and 1Ad) generated from the nucleotide sequence deduced from the $NH_2$-terminal amino acid sequence of TBP-I (FIG. 1Aa) were used for the screening of cDNA libraries. Initial screenings were carried out with 48-fold degenerated, 26-mers into which deoxyinosine was introduced, wherever the codon ambiguity allowed for all four nucleotides (FIG. 1Ab). The validity of positive clones was examined by testing their hybridization to two mixed 17-mer nucleotide sequences containing 96 and 128 degeneracies, corresponding to two overlappings amino acid sequences which constitute part of the sequencers to which the 26-base probes correspond (FIGS. 1Ac and d). An oligonucleotide probe corresponding to a sequence located close to the 5' terminus of the longest of the partial cDNA clones isolated with the degenerated probes (nucleotides 478-458 in FIG. 1D) was applied for further screening cDNA libraries for a full length cDNA clone. $^{32}$P-labeling of the probes, using T4 polynucleotide kinase, plating of the phages in lawns of bacteria, their screening with the radiolabelled probes, isolation of the positive clones and subcloning of their cDNA inserts were carried out using standard procedures (Sambrook, J., et al., (1989) *Molecular Cloning, A Laboratory Manual*. Cold Spring Harbor Laboratory Press).

c) Nucleotide sequencing of the cDNA clones cDNA inserts isolated from positive lambda GT11 recombinant phases were subcloned into the pBluescript KS(-) vector. Inserts found in lambda ZAP phages were rescued by excising the plasmid pBluescript SK(-) in them, using the R408 helper phage (Short, J. M., et al., (1988) Nucl.Acids Res. 16, pp. 7583–7600). DNA sequencing in both directions was done by the dideoxy chain termination method. Overlapping deletion clones of the cDNAs were generated, in both orientations, by digestion of the cDNA with exonuclease III ("Erase a base" kit, Promega Biotec, Madison, Wis.). Single stranded templates derived from these clones using the R408 phage were sequenced with a T7 DNA polymerase sequencing system (Promega).

d) Constitutive expression of the type I human TNF-R in CHO cells

The E13 insert was introduced into a modified version of the pSVL expression vector. This construct was transfected, together with the pSV2-DHFR plasmid which contains the DHFR cDNA, into DHFR deficient CHO cells, using the calcium phosphate precipitation method. Transfection with a recombinant pSVL vector which contained the E13 insert in the inverse orientation served as a control. Cells expressing the DNFR gene were selected by growth in nucleotide-free HEX alpha medium containing fetal calf serum which had been dialyzed against phosphate buffered saline. Individual clones were picked out and then further selected for amplification of the transfected cDNAs by growth in the presence of 500 nM sodium methotrexate.

e) Detection of surface-expressed type I TNF-R in the CHO cells

Binding of radiolabelled human rTNF to cells (seeded in 15 mm tissue culture plates at a density of 2.5×10$^5$ cells/plate) was quantitated as described before (Holtmann, H. and Wallach, D. (1987) J.Immunol. 139, pp. 1161–1167).

To examine the binding of monoclonal antibodies against TBP-I to CHO cells, the cells were detached by incubation in phosphate buffered saline (PBS: 140 mM NaaCl, 1.5 mM KH$_2$PO$_4$; 8 mM Na$_2$HPO$_4$, 2.7 m KCl, 0.5 m MgCl$_2$, 0.9 m CaCl$_2$), containing 5 mM EDTA and then incubated for 45 min. at 0° C. with 50 µg/ml of the test monoclonal antibody in PBS containing 0.5% bovine serum albumin, and 15 mM sodium azide (PBS/BSA). After washing the cells with PBS/BSA they were incubated further for 30 min. at 0° C. with FITC labelled, affinity purified goat antibody to the F(ab) fragment of mouse ISG (1:20 in PBS/BSA) (Bio-Makor, Israel) and then analyzed by determining the intensity of fluorescence in samples of 10$^4$ cells using the Becton Dickinson fluorescence activated cell sorter 440. Three monoclonal antibodies to TBP-I, clones 17,18 and 20, shown by cross competition analysis to recognize four spatially distinct epitopes in the TBP-I molecule U.S. Pat. No. 5,359,037 and, as a control, a monoclonal antibody against TNF-α (all purified from ascitic fluids by ammonium sulphate precipitation and of the ISG2 isotype), were used.

f) Quantitation of the soluble form of the type I TNF-R by ELISA

A sensitive enzyme linked immunosorbent assay was set up using TBP-I-specific monoclonal and polyclonal antibodies in a sandwich technique. Immunoglobulins of the anti-TBP-I mAb clone 20 U.S. Pat. No. 5,359,037 were adsorbed to 96-well ELISA plates (maxisorp, Nunc, Denmark) by incubation of the plates for 2 h. at 37° C. with a solution of 25 µg/ml of the antibody in PBS. After incubating the wells further for 2 h. at 37°°C. with a solution containing phosphate buffered saline, 1% BSA, 0.02% NaN$_3$ and 0.05% Tween 20 (blocking solution) to block nonspecific further binding of protein, tested samples were applied in aliquots of 50 µl/well. The plates were then incubated for 2 h. at 37° C., rinsed 3 times with PBS supplemented with 0.05% Tween 20 (washing solution) and rabbit polyclonal antiserum against TBP-I, diluted 1:500 in blocking solution, was added to the wells. After further incubation for 12 h. at 4° C. the plates were rinsed again and incubated for 2 h. with horse raddish peroxidase-conjugated purified goat anti-rabbit IgG. The assay was developed using 2,2'-azino-bis (3-ethylbenzthiazoline-6 sulfonic acid) as a substrate (Sigma). The enzymatic product was determined colorimetrically at 600 nm. Pure TBP-I served as a standard.

g) Detection of a soluble form of the type I TNF-R in the growth medium of the transfected CHO cells and its analysis by reversed phase HPLC The amounts of the soluble form of the type I TNF-R in samples of the medium of the tested CHO cells, collected 48 h after medium replacement, were determined by the immunoassay described above. For analysis of the soluble receptor by reversed phase HPLC the CHO cells were cultured for 48 h. in serum-free medium (nucleotide-free MEM α). The medium samples were concentrated 100-fold by ultrafiltration on an Amicon PM5 membrane and 100 µl aliquots were then applied to an Aquapore RP300 column (4.5×30 mm, Brownlee Labs) preequilibrated with 0.3% aqueous trifluoroacetic acid. The column was washed with this solution at a flow rate of 0.5 ml/min until all unbound proteins were removed, and then eluted with a gradient of acetonitrile concentration in 0.3% aqueous trifluoroacetic acid, as described before (Engelmann, H., et al. (1989) J.Biol.Chem. 264, pp. 11974–11980), Fractions of 0.5 ml were collected and, after concentration in vacuo, were neutralized with 1M HEPES buffer pH 9.0. Amounts of soluble type I TNF-R in the fractions were determined by ELISA and the concentration of protein by the fluorescamine method.

EXAMPLE 2 a) Cloning of the cDNA for the Type I TNF-R

To clone the cDNAs which code for the TNF-binding protein, TBP-I, and its related TNF receptor, several cDNA libraries were screened, using 3 overlapping oligonucleotide probes designed on the basis of the NH$_2$-terminal amino acid sequence of TBP-I (FIG. 1A). In a lambda GT11 library derived from the mRNA of human colon (randomly primed, Clontech, Palo Alto, Calif.), four recombinant phages which hybridized with the three probes were detected. The inserts in these four phages were similar in size, and were found to overlap by restriction mapping and sequence analysis.

Complete analysis of the sequence of the longest of the four (C2 in FIG. 1B, deposited on 6.12.1989 with the Collection Nationale de Cultures de Microorganismes (C.N.C.M.), Paris, France, Accession No. I-917) revealed an open reading frame, extended over its entire length. A polypeptide chain encoded in this reading frame fully matches the $NH_2$-terminal amino acid sequence of TBP-I. Neither an initiation nor a stop codon was found in the C2 insert. Rescreening the colon cDNA library, using another probe corresponding to a sequence found in C2 (see Example 1: Procedures), yielded several other recombinant phages containing inserts that overlap with the C2 insert. However, none of them provided further sequence information on the cDNA in the 5' or the 3' direction. In a lambda ZAP cDNA library derived from the mRNA of CEM lymphocytes (Oligo dT and randomly primed, Clontech) five phages hybridizing with this probe were detected, which contained significantly longer inserts than C2.

The longest insert (E13, FIG. 1B) was sequenced in its entirety (FIG. 1D) and was found to contain the C2 sequence (nucleotides 346-1277 in FIG. 1D) within one long open reading frame of 1365 bp, flanked by untranslated regions of 255 and 555 nucleotides at its 5' and 3' ends, respectively. The potential ATG initiation site, occurring at positions 256-258 in the nucleotide sequence (SEQ ID NO:2) (denoted by an asterisk in FIG. 1D) is preceded by an upstream in-frame termination codon at bases 244-246. The start location is in comformity with one of the possible alternatives for the translation initiation consensus sequence (GGCATGG, nucleotides 253-259).

There is no characteristic poly(A) addition signal near the 3' end of the cDNA. The sequence ACTAAA, at nucleotides 2045-2050, may serve as an alternative to this signal, but with low efficiency. At nucleotides 1965-2000, there are six consecutive repeats of the sequence G(T)n (n varying between 4 and 8).

The size of the protein encoded by the cDNA (about 50 kD) is significantly larger than that of TBF-I. A hydropathy index computation of the deduced amino acid sequence of the protein (FIG. 1C) revealed two major hydrophobic regions (see round-ended boxes in FIG. 1D). One, at its $NH_2$-terminus, is apparently the signal peptide whose most likely cleavage site lies between the glycine and isoleucine residues designated in FIG. 1D as −1 and +1 respectively. The other major hydrophobic domain, located between residues 191 and 213, is flanked at both ends by several charged amino acids, characteristic of a membrane anchoring domain. As in several other transmembrane proteins, the amino acids confining the hydrophobic domain at its COOH-terminal are basic. The transmembrane domain bisects the predicted protein into almost equally sized extracellular and intracellular domains.

The extracellular domain has 3 putative sites for asparagine-linked glycosylation (overlined in FIG. 1D). Assuming that the amount of oligosaccharides in the extracellular domain is similar to that reported as present in TBP-I (Seckinger, P., et al., (1989b) Cytokine I, 149 (an abstract)), the molecular size of the mature protein is very similar to that estimated for the type I receptor (about 58 kD) (Hohmann, M. P., et al., (1989) J.Biol.Chem. 264, pp. 14927–14934).

b) Features by the predicted amino acid sequence in the Type I TNF-R and relationship to the structure of TBP-I and TBP-II The amino acid sequence of the extracellular domain of the protein encoded by the E13 cDNA fully matches several sequences of amino acids determined in TBP-I (Table I). It contains the $NH_2$-terminal amino acid sequence of TBP-I at amino acids 20-32 (compare FIG. 1D and FIG. 1Aa), a sequence corresponding to the COOH terminus of TBP-I at amino acid 178-180; and, also, adjacent to the first methionine located further downstream in the encoded protein, a sequence which is identical to the $NH_2$-terminal amino acid sequence of a cyanogenbromide cleavage fragment of TBP-I (broken lines in FIG. 1D). There is also a marked similarity in amino acid composition between the extracellular domain of the receptor and TBP-I (Table II).

The most salient feature of this amino acid composition is a very high content of cystein residues (shown boxed in FIG. 1D). The positioning of the cystein residues as well as of other amino acids within the extracellular domain displays a four-fold repetition pattern (underlined in FIG. 1D). The amino acid sequence within the extracellular domain of the TNF-R, which corresponds to the COOH terminal sequence of TBP-I (see Table I and FIG. 4), is located at the COOH terminus of the cystein-rich repeat region. The sequence corresponding to the $NH_2$ terminal sequence of TBP-I corresponds to a sequence located a few amino acids upstream of the $NH_2$ terminal end of this region (broken lines in FIG. 1D) in the extracellular domain.

In contrast to the identity of amino acid sequences between TBP-I and the extracellular domain of the type I TNF receptor, sequences examine in the soluble form of the type II TNF-R (TBP-II, Table I) were not identical to any sequence in the type I TNF-R. This finding is expected, considering the lack of immunological crossreactivity between the two receptors (Engelmann, H., et al., (1990) J.Biol.Chem. 265, pp. 1531–1535).

In contrast to the very high content of cystein residues in the putative extracellular domain of the type I TNF-R, there are only 5 cystein residues in the intracellular domain. Between the two which are proximal to the transmembrane domain (positions 227 and 283), extends a stretch of 55 amino acids which is rich in proline residues (15% of the residues) and even richer in serine and threonine residues (36%), most located very close to or adjacent to each other.

EXAMPLE 3
Expression of the type I TNF-R cDNA

To explore the relation between the protein encoded by the E13 cDNA and TBP-I further, this protein was expressed in CHO cells. The E13 cDNA was introduced into an expression vector and was cotransfected with a recombinant vector containing the dihydrofolate reductase (DHFR) cDNA into DNFR-deficient cells. After selection by growth in a nucleotide-free medium, individual clones were amplified by growth in the presence of methotrexate. A number of clones which react with several monoclonal antibodies that bind to spatially distinct epitopes in TBP-I were detected (FIG. 2). Expression of the protein was correlated with an increase in specific binding of human TNF to the cells (Table III).

Applying a sensitive immunoassay for TBP-I in which polyclonal antibodies and a monoclonal antibody against this protein were employed, (Procedures, Example 1f) in the medium of CHO cells which express the human TNF-R on their surface, also a soluble form of the protein could be detected (Table III). All of five different CHO clones which expressed the TNF-RT produced this soluble protein. Several other transfected clones which did not express the cell surface receptor did not produce its soluble form either. When analyzed by reversed phase HPLC, the CHO-produced soluble TNF-R eluted as a single peak, with a retention time identical to that of TBF-I (FIG. 3).

EXAMPLE 4
Cloning of the cDNA encoding TBP-I and expression of TBP-I in Chinese Hamster Ovary (CHO) cells In order to obtain plasmids suitable for efficient expression of the DNA encoding a soluble domain of the type I TNF receptor in mammalian cells, the gene from position 256 to position 858 of the DNA sequence shown in FIG. 1D (SEQ ID NO:1), was cloned in two expression vectors: in one plasmid, gene expression was under the SV40 early gene promoter; in the second plasmid, gene expression was under the regulation of the cytomegalovirus (CMV) promoter. These vectors were introduced into CHO cells by $CaPO_4$ coprecipitation with a plasmid DHFR selectable genetic marker.

Construction of Expression Vectors
1) SV40 Early Promoter-TBP-I fusion: Plasmid pSV-TBP Constitutive expression of TBP-I can be achieved by using an expression vector that contains the DNA sequence coding for TBP-I fused to the strong SV40 early gene promoter (FIG. 5).

Step 1

A DNA fragment coding for TBP-I, including its signal peptide and extending to amino acid 180 (nucleotides 256-858 of SEQ ID NO:1) was prepared by PCR amplification. For amplification two oligonucleotides were used as primers: the 5' end primer contains the sequence coding for the first seven amino acids of the signal peptide, preceded by six nucleotides (SEQ ID NO:6); the 3' end oligonucleotide contains the sequence coding for amino acid residues 174 through 180 followed by two stop codons (TGA and TAA) (SEQ ID NO:7).

The conditions for PCR amplification are the following:

|  | Temperature °C. | Time min |
|---|---|---|
| 1 cycle | 94 | 6 |
|  | 50 | 2 |
|  | 72 | 4 |
| 30 cycles | 94 | 1 |
|  | 50 | 2 |
|  | 72 | 4 |
| 1 cycle | 94 | 1 |
|  | 50 | 2 |
|  | 72 | 12 |

Step 2

After sequence verification, the amplified DNA fragment was cloned into the HindII restriction site of plasmid pGEM-1 by blunt end ligation. Plasmids pTSP-16 and pTBP-17 are the two plasmids obtained in this way and they differ in the orientation of the TSP-I insert with respect to the cloning vector.

Step 3

The DNA fragment containing TBP-I was excised from plasmid pBP-17 using the two adjacent restriction sites HindIII (at the 5' end) and BamHI (at the 3' end).

Step 4

Finally, this fragment was cloned between the HindIII and the BalI restriction sites of the expression vector pSVE3. The resulting plasmid is called pSV-TBP (FIG. 5).

2) CMV promoter-TBP-I fusion: plasmid pCMV-TBP

Alternatively, constitutive expression of TBP-I can be achieved by using an expression vector that contains the DNA sequence coding for TBP-I fused to the CMV promoter (FIG. 5).

The first two steps for the construction of the CMV based vector are identical to the ones described for the construction of the SV40-TBPI fusion plasmid, as described above.

Step 3

The DNA fragment containing TBP-I was excised from plasmid pTBP-17 using the two adjacent restriction sites HindIII (at the 5' end) and XbaI (at the 3' end).

Step 4

Finally, this fragment was cloned between the HindIII and the XbaI restriction sites of the expression vector Rc/CMV. The resulting plasmid is called pCMV-TBP.

Expression of Human TBP-I in CHO Cells

CHO cells CHO-K1 DHFR⁻, lacking DHFR activity, were transformed by $CaPO_4$ coprecipitation with a 12:1 mixture of uncut pSV-TBP DNA (73 μg) and mpSV2DHFR (6 μg) DNA, the latter being the selectable marker. Alternatively, CHO cells were transformed with a 5:1 mixture of PCMV-TBP (30 μg) and mpSV2DHFR (5 μg).

Cells were grown in nutrient mixture F12 (Gibco) with 10% fetal calf serum (FCS) at 37° C. in 5% $CO_2$. For DNA transfection, $5 \times 10^x$ cells were cultured for one day in 9 cm plates. A $CaPO_4$-DNA coprecipitate was prepared by mixing plasmid DNAs, dissolved in 0.45 ml of Tris-HCl pH 7.9, 0.1 mM EDTA with 0.05 ml of 2.5M $CaCl_2$; therafter, 0.5 ml of 280 mM $Na_2PO_4$, 50 mM Hepes buffer pH 7.1 was added with gentle mixing. The mixture was kept for 30–40 minutes at room temperature in order to form the precipitate. After adding the $CaPO_4$-DNA to the cells and leaving the cells at room temperature for 30 min, 9 ml of nutrient mixture F12, 10% FCS were added and the cultures returned to the $CO_2$ incubator for 4 hours. Medium was removed and the cells were osmotically shocked with 10% glycerol in F12 for 4 min. After 48 hours of growth in non-selective medium, the cells were then trypsinized and subcultured 1:10 into selective medium, composed of Dulbeoco's modified Eagle's medium (DMEM) (H21, Gibco), 150 μg/ml proline, and 10% FCS which had been extensively dialyzed against phosphate-buffered saline (PBS). In some cases, MEM alpha medium without nucleotides (F20, Gibco) was used. The cultures were kept at 37° C. and 10% $CO_2$ and the medium was changed every 3–4 days. Clones were isolated after about 15 days, trypsinized, and grown to mass cultures.

Transformants able to grow in medium lacking thymidine (DMEM with dialyzed serum) were obtained. Culture supernatants of individual transformant clones or culture supernatant of mixed populations were screened for human TBP-I by measuring the level of secreted protein by the enzyme linked immunoassay described in Example 1f. TBP-I levels of up to 10 ng/ml were detected in culture supernatants of mixed cells populations.

This example shows that TBP-I or a similar soluble protein can be obtained also by transfection of mammalian cells with a DNA encoding the soluble domain of the type I TNF receptor.

EXAMPLE 5

Expression of TBP-I in *E. coli*

For expression of TBP-I in *E. coli*, peptide ace coding for the signal peptide and for the first 19 aminoacids (Arg) must be removed (FIG. 1D). Moreover, the Asp residue must be preceded by a Met residue. The desired fragment is then cloned into the expression vector pKK223-3 that contains the hybrid tryp-lac promoter. To achieve this goal plasmid pTBF-16 (FIG. 5) is cut with the two unique restriction sites StyI and HindIII. StyI restriction site is C/CAAGG and, therefore, it cuts after Pro24. HindIII restriction site is located in the polylinker of the plasmid and downstream from the two added stop codons that follow Asn180 (FIG. 5).

The resulting DNA fragment, coding for TBP-I, has an intact 3' end and a truncated 5' end, where the sequence preceding the StyI site and coding for Asp-Ser-Val-Cys-Pro, (amino acids 20-24 of SEQ ID NO:2) has been removed.

For cloning of the StyI-HindIII fragment into the expression vector pKK223-3, the following couple of synthetic oligonucleotides are used:

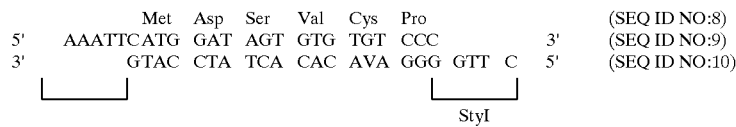

```
              Met  Asp  Ser  Val  Cys  Pro
5'  AAATTCATG  GAT  AGT  GTG  TGT  CCC           3'    (SEQ ID NO:8)
3'          GTAC  CTA  TCA  CAC  AVA  GGG  GTT  C  5'  (SEQ ID NO:9)
                                                        (SEQ ID NO:10)
                                    StyI
```

One end of this double stranded oligonucleotide is an EcoRI restriction site. This end is ligated to the EcoRI site of plasmid pKK223-3, located downstream to the tryp-lac promoter. The second end of the double stranded oligonucleotide is a StyI restriction site to be ligated to the StyI of the TBP-I DNA fragment.

The remainder of the sequence is such that the codons coding for the first five amino acids are restored and that an additional Met codon is added in front of Asp20. The expression vector is obtained by ligation of plasmid pKK223-3, digested with EcoRI and HindIII, to the double-stranded synthetic oligonucleotide and to the StyI-HindIII TBPI fragment.

*E.coli* cells are transfected with this expression vector in order to produce TBP-I.

TABLE II

Similarily of the amino acid compositions of the TNF binding protein TBPI and a corresponding region in the extracellular domain of the TNF-R (type I)

| | mol/100 mol of amino acids | |
|---|---|---|
| Amino acid | TBPI* | Residues 20–180 in the extracellular domain** |
| Ala 1.7 | 1.2 | |
| Cys | 12.8 | 14.9 |
| Asp + Asn | 10.0 | 11.1 |
| Glu + Gln | 13.0 | 12.4 |
| Phe | 3.2 | 3.1 |

TABLE 1

Amino Acid Sequences of TBP I and TPB II

| TBP I: | | 1 | 2 | 3 | 4 | 5 | 6 | 7 | 8 | 9 | 10 | 11 | 12 | 13 | 14 | 15 |
|---|---|---|---|---|---|---|---|---|---|---|---|---|---|---|---|---|
| CNBr-1 (=N-terminus) | NH₂ | Asp | Ser | Val | Cys | Pro | Gln | Gly | Lys | Tyr | Ile | His | Pro | Gln | — | |
| | | (Seq. ID No.: 2, amino acids 41–53) | | | | | | | | | | | | | | |
| CNBr-2 | NH₂ | Gly | Gln | Val | Glu | Ile | Ser | Ser | Cys | Thr | Val | Asp | Arg | Asp | Thr | Val |
| | | (Seq. ID No.: 2, amino acids 110–124) | | | | | | | | | | | | | | |
| C-terminus | | Ile | Glu | Asn | COOH | | | | | | | | | | | |
| TBP II: | | 1 | 2 | 3 | 4 | 5 | 6 | 7 | 8 | 9 | 10 | 11 | 12 | 13 | 14 | 15 |
| N-terminus (Seq. ID. No. 11) | NH₂ | Ala | Gln | Val | Ala | Phe | Thr | Pro | Tyr | Ala | Pro | Glu | Pro | Gly | Ser | Thr |
| | | Cys | Arg | Leu | Arg | Glu | Tyr | Tyr | - | | | | | | | |
| TRP 35 (Seq. ID. No. 12) | NH₂ | Leu | Cys | Ala | Pro | Leu | Arg | Lys | | | | | | | | |
| TRP 39/1 (Seq. ID. No. 13) | NH₂ | Cys | Arg | Pro | Gly | Phe | Gly | Val | Ala | Arg | | | | | | |
| TRP 39/2 (Seq. ID. No. 14) | NH₂ | Glu | Tyr | Tyr | Asp | Gln | Thr | Ala | Gln | Met | Cys | Cys | — | | | |
| TRP 44/1 (Seq. ID. No. 15) | NH₂ | Glu | Tyr | Tyr | Asp | Gln | Thr | Ala | Gln | Met | Cys | Cys | Ser | — | | |
| TRP 44/2 (Seq. ID. No. 16) | NH₂ | Ser | Cys | Gly | Pro | Ser | Tyr | Pro | Asp | — | | | | | | |
| TRP 46/1 (Seq. ID. No. 17) | NH₂ | Phe | Thr | Pro | Tyr | Ala | Pro | Glu | Pro | Gly | Ser | Thr | Cys | Arg | | |
| TRP 46/2 (Seq. ID. No. 18) | NH₂ | Leu | Arg | Glu | Tyr | Tyr | Asp | Gln | Thr | Ala | Gln | Met | Cys | Cys | — | |
| TRP 50 (Seq. ID. No. 18) | NH₂ | Leu | Arg | Glu | Tyr | Tyr | Asp | Gln | Thr | Ala | Gln | Met | Cys | Cys | — | |
| TRP 54/1 (Seq. ID. No. 19) | NH₂ | Pro | Gly | Trp | Tyr | Cys | Ala | Leu | Ser | Lys | | | | | | |
| TRP 54/2 (Seq. ID. No. 20) | NH₂ | Ala | Gln | Val | Ala | Phe | Thr | Pro | Tyr | Ala | Pro | Glu | Pro | Gly | Ser | Thr |
| | | Cys | Arg | | | | | | | | | | | | | |
| TRP 53/1 (Seq. ID. No. 21) | NH₂ | Val | Ala | Phe | Thr | Pro | Tyr | Ala | Pro | Glu | Pro | Gly | Ser | Thr | Cys | Arg |
| TRP 53/2 (Seq. ID. No. 22) | NH₂ | Cys | Arg | Pro | Gly | Phe | Gly | Val | Ala | Arg | | | | | | |
| TRP 60 (Seq. ID. No. 23) | NH₂ | Ile | Cys | Thr | Cys | Arg | Pro | Gly | Trp | Tyr | Cys | Ala | Leu | Ser | — | |
| TRP 62 (Seq. ID. No. 24) | NH₂ | Pro | Gly | Thr | Glu | Thr | Ser | Asp | Val | Val | Cys | Lys | Pro | Cys | Ala | Pro |
| | | Gly | Thr | Phe | Ser | Lys | | | | | | | | | | |
| TRP 65 (Seq. ID. No. 24) | NH₂ | Pro | Gly | Thr | Glu | Thr | Ser | Asp | Val | Val | Cys | Lys | Pro | Cys | Ala | Pro |
| | | Gly | Thr | Phe | Ser | Lys | | | | | | | | | | |
| TRP 67 (Seq. ID. No. 25) | NH₂ | Cys | Arg | Pro | Gly | Phe | Gly | Val | Ala | Arg | Pro | Gly | Thr | Glu | Thr | Ser |
| | | Asp | Val | Val | Cys | Lys | | | | | | | | | | |
| TRP 84 (Seq. ID. No. 26) | NH₂ | Thr | Ser | Asp | Thr | Val | Cys | Asp | Ser | Cys | Glu | Asp | Ser | Thr | Tyr | Thr |
| | | Gln | Leu | Trp | — | | | | | | | | | | | |

TABLE II-continued

Similarily of the amino acid compositions of the TNF binding protein TBPI and a corresponding region in the extracellular domain of the TNF-R (type I)

| | mol/100 mol of amino acids | |
|---|---|---|
| Amino acid | TBPI* | Residues 20–180 in the extracellular domain** |
| Gly | 0.3 | 5.6 |
| Ills | 4.4 | 4.3 |
| Ile | 2.8 | 2.5 |
| Lys | 0.2 | 6.2 |
| Leu | 8.0 | 6.8 |
| Met | 0.4 | 0.0 |
| Pro | 3.8 | 3.1 |
| Arg | 4.7 | 4.3 |
| Ser | 8.1 | 9.3 |
| Thr | 0.1 | 0.2 |
| Val | 4.2 | 4.3 |
| Trp | — | 0.0 |
| Tyr | 2.4 | 3.1 |

*According to Olssen et al., 1980
**Residue 20 corresponds to the $NH_2$-terminal amino acid of TBPI, Residue 180 is the COOH-terminal residue of TBPI.

TABLE III

Expression of the cell surface and soluble forms of human type I TNF-R in CHO cells

| CHO cell clone | Specific binding of TNF (CPM/$10^4$ cells) | cells expressing human cell surface TNF-R (% fluorescent cells) | human soluble type I TNF receptors (pg/ml) |
|---|---|---|---|
| nontranfected | 180 ± 45 | <1% | <0.03 |
| CO | 175 ± 50 | <1% | <0.03 |
| R-10 | 550 ± 60 | 73% | 30 |
| R-18 | 610 ± 40 | 89% | 40 |

The R-10 and R-18 clones consist of cells transfected with a recombinant expression vector containing E13 eDNA. C-6 cells were transfected with a control vector (see FIG. 3). Binding of radiolabelled TNF to the cells was determined in particular examples. Detection of immunoractive receptors on the surface of the cells was carried out using combined 17, 18, 20 , and 30 mol TBPI monoclonal antibodies. Results are expressed as percentage of fluorescent cells (background values, obtained by staining the cells with an anti-TNF monoclonal antibody, are subracted). For other details, see Materials and Methods.

---

We claim:

1. A method for the production of a soluble recombinant protein having the tumor necrosis factor binding characteristics of human tumor necrosis factor binding protein I (TBP-I), which comprises:

(i) transfecting mammalian cells with an expression vector comprising a DNA molecule encoding the whole human type I TNF receptor;

(ii) culturing the transfected cells, whereby the desired protein is produced and secreted into the medium; and (iii) recovering the desired protein from the medium.

2. A method according to claim 1 wherein the DNA molecule encoding the whole type I TNF receptor is the cDNA having the sequence SEQ ID NO:1.

3. A method according to claim 2 wherein the cDNA is introduced into an expression vector and is cotransfected with a recombinant vector containing the dihydrofolate reductase (DHFR) cDNA into DHFR-deficient chinese hamster ovary (CHO) cells.

4. A method according to claim 3 wherein the cells are selected by growth in a nucleotide-free medium, individual clones are amplified by growth in the presence of methotrexate and the soluble protein secreted into the medium is detected by reaction with monoclonal and polyclonal antibodies raised against TBP-I.

5. A method according to claim 1 wherein the soluble protein secreted into the medium shows a retention time identical to that of TBP-I when analyzed by reversed phase HPLC.

6. A method according to claim 1 for the production of human TBP-I.

7. A method in accordance with claim 1 wherein said soluble recombinant protein having the tumor necrosis factor binding characteristics of human TBP-I consists of a protein extending from any one of residues 1-20 through any one of residues 180-182 of SEQ ID NO:2.

* * * * *

SEQUENCE LISTING ( 1 ) GENERAL INFORMATION:

( i i i ) NUMBER OF SEQUENCES: 26

( 2 ) INFORMATION FOR SEQ ID NO:1:

( i ) SEQUENCE CHARACTERISTICS:
        ( A ) LENGTH: 2175 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 256..1620

( i x ) FEATURE:
        ( A ) NAME/KEY: mat_peptide
        ( B ) LOCATION: 319..1620

( x i ) SEQUENCE DESCRIPTION: SEQ ID NO:1:

```
CGGCCCAGTG  ATCTTGAACC  CCAAAGGCCA  GAACTGGAGC  CTCAGTCCAG  AGAATTCTGA        60

GAAAATTAAA  GCAGAGAGGA  GGGGAGAGAT  CACTGGGACC  AGGCCGTGAT  CTCTATGCCC       120

GAGTCTCAAC  CCTCAACTGT  CACCCCAAGG  CACTTGGAC   GTCCTGGACA  GACCGAGTCC       180

CGGGAAGCCC  CAGCACTGCC  GCTGCCACAC  TGCCCTGAGC  CCAAATGGGG  GAGTGAGAGG       240

CCATAGCTGT  CTGGC ATG GGC  CTC TCC  ACC  GTG  CCT  GAC  CTG  CTG  CTG  CCG      291
```

-continued

|     |     |     |     |     | Met | Gly | Leu | Ser | Thr | Val | Pro | Asp | Leu | Leu | Leu | Pro |     |
|     |     |     |     |     | -21 | -20 |     |     |     | -15 |     |     |     |     |     | -10 |     |

| CTG | GTG | CTC | CTG | GAG | CTG | TTG | GTG | GGA | ATA | TAC | CCC | TCA | GGG | GTT | ATT | 339 |
| Leu | Val | Leu | Leu | Glu | Leu | Leu | Val | Gly | Ile | Tyr | Pro | Ser | Gly | Val | Ile |     |
|     |     |     |     | -5  |     |     |     |     | 1   |     |     |     |     | 5   |     |     |

| GGA | CTG | GTC | CCT | CAC | CTA | GGG | GAC | AGG | GAG | AAG | AGA | GAT | AGT | GTG | TGT | 387 |
| Gly | Leu | Val | Pro | His | Leu | Gly | Asp | Arg | Glu | Lys | Arg | Asp | Ser | Val | Cys |     |
|     |     | 10  |     |     |     |     | 15  |     |     |     |     | 20  |     |     |     |     |

| CCC | CAA | GGA | AAA | TAT | ATC | CAC | CCT | CAA | AAT | AAT | TCG | ATT | TGC | TGT | ACC | 435 |
| Pro | Gln | Gly | Lys | Tyr | Ile | His | Pro | Gln | Asn | Asn | Ser | Ile | Cys | Cys | Thr |     |
|     | 25  |     |     |     |     | 30  |     |     |     |     | 35  |     |     |     |     |     |

| AAG | TGC | CAC | AAA | GGA | ACC | TAC | TTG | TAC | AAT | GAC | TGT | CCA | GGC | CCG | GGG | 483 |
| Lys | Cys | His | Lys | Gly | Thr | Tyr | Leu | Tyr | Asn | Asp | Cys | Pro | Gly | Pro | Gly |     |
| 40  |     |     |     |     | 45  |     |     |     |     | 50  |     |     |     |     | 55  |     |

| CAG | GAT | ACG | GAC | TGC | AGG | GAG | TGT | GAG | AGC | GGC | TCC | TTC | ACC | GCT | TCA | 531 |
| Gln | Asp | Thr | Asp | Cys | Arg | Glu | Cys | Glu | Ser | Gly | Ser | Phe | Thr | Ala | Ser |     |
|     |     |     |     | 60  |     |     |     |     | 65  |     |     |     |     | 70  |     |     |

| GAA | AAC | CAC | CTC | AGA | CAC | TGC | CTC | AGC | TGC | TCC | AAA | TGC | CGA | AAG | GAA | 579 |
| Glu | Asn | His | Leu | Arg | His | Cys | Leu | Ser | Cys | Ser | Lys | Cys | Arg | Lys | Glu |     |
|     |     |     |     | 75  |     |     |     |     | 80  |     |     |     |     | 85  |     |     |

| ATG | GGT | CAG | GTG | GAG | ATC | TCT | TCT | TGC | ACA | GTG | GAC | CGG | GAC | ACC | GTG | 627 |
| Met | Gly | Gln | Val | Glu | Ile | Ser | Ser | Cys | Thr | Val | Asp | Arg | Asp | Thr | Val |     |
|     |     | 90  |     |     |     |     | 95  |     |     |     |     | 100 |     |     |     |     |

| TGT | GGC | TGC | AGG | AAG | AAC | CAG | TAC | CGG | CAT | TAT | TGG | AGT | GAA | AAC | CTT | 675 |
| Cys | Gly | Cys | Arg | Lys | Asn | Gln | Tyr | Arg | His | Tyr | Trp | Ser | Glu | Asn | Leu |     |
|     | 105 |     |     |     |     | 110 |     |     |     |     | 115 |     |     |     |     |     |

| TTC | CAG | TGC | TTC | AAT | TGC | AGC | CTC | TGC | CTC | AAT | GGG | ACC | GTG | CAC | CTC | 723 |
| Phe | Gln | Cys | Phe | Asn | Cys | Ser | Leu | Cys | Leu | Asn | Gly | Thr | Val | His | Leu |     |
| 120 |     |     |     |     | 125 |     |     |     |     | 130 |     |     |     |     | 135 |     |

| TCC | TGC | CAG | GAG | AAA | CAG | AAC | ACC | GTG | TGC | ACC | TGC | CAT | GCA | GGT | TTC | 771 |
| Ser | Cys | Gln | Glu | Lys | Gln | Asn | Thr | Val | Cys | Thr | Cys | His | Ala | Gly | Phe |     |
|     |     |     |     | 140 |     |     |     |     | 145 |     |     |     |     | 150 |     |     |

| TTT | CTA | AGA | GAA | AAC | GAG | TGT | GTC | TCC | TGT | AGT | AAC | TGT | AAG | AAA | AGC | 819 |
| Phe | Leu | Arg | Glu | Asn | Glu | Cys | Val | Ser | Cys | Ser | Asn | Cys | Lys | Lys | Ser |     |
|     |     | 155 |     |     |     |     | 160 |     |     |     |     | 165 |     |     |     |     |

| CTG | GAG | TGC | ACG | AAG | TTG | TGC | CTA | CCC | CAG | ATT | GAG | AAT | GTT | AAG | GGC | 867 |
| Leu | Glu | Cys | Thr | Lys | Leu | Cys | Leu | Pro | Gln | Ile | Glu | Asn | Val | Lys | Gly |     |
|     |     | 170 |     |     |     |     | 175 |     |     |     |     | 180 |     |     |     |     |

| ACT | GAG | GAC | TCA | GGC | ACC | ACA | GTG | CTG | TTG | CCC | CTG | GTC | ATT | TTC | TTT | 915 |
| Thr | Glu | Asp | Ser | Gly | Thr | Thr | Val | Leu | Leu | Pro | Leu | Val | Ile | Phe | Phe |     |
| 185 |     |     |     |     | 190 |     |     |     |     | 195 |     |     |     |     |     |     |

| GGT | CTT | TGC | CTT | TTA | TCC | CTC | CTC | TTC | ATT | GGT | TTA | ATG | TAT | CGC | TAC | 963 |
| Gly | Leu | Cys | Leu | Leu | Ser | Leu | Leu | Phe | Ile | Gly | Leu | Met | Tyr | Arg | Tyr |     |
| 200 |     |     |     |     | 205 |     |     |     |     | 210 |     |     |     |     | 215 |     |

| CAA | CGG | TGG | AAG | TCC | AAG | CTC | TAC | TCC | ATT | GTT | TGT | GGG | AAA | TCG | ACA | 1011 |
| Gln | Arg | Trp | Lys | Ser | Lys | Leu | Tyr | Ser | Ile | Val | Cys | Gly | Lys | Ser | Thr |     |
|     |     |     |     | 220 |     |     |     |     | 225 |     |     |     |     | 230 |     |     |

| CCT | GAA | AAA | GAG | GGG | GAG | CTT | GAA | GGA | ACT | ACT | ACT | AAG | CCC | CTG | GCC | 1059 |
| Pro | Glu | Lys | Glu | Gly | Glu | Leu | Glu | Gly | Thr | Thr | Thr | Lys | Pro | Leu | Ala |     |
|     |     |     | 235 |     |     |     |     | 240 |     |     |     |     | 245 |     |     |     |

| CCA | AAC | CCA | AGC | TTC | AGT | CCC | ACT | CCA | GGC | TTC | ACC | CCC | ACC | CTG | GGC | 1107 |
| Pro | Asn | Pro | Ser | Phe | Ser | Pro | Thr | Pro | Gly | Phe | Thr | Pro | Thr | Leu | Gly |     |
|     |     | 250 |     |     |     |     | 255 |     |     |     |     | 260 |     |     |     |     |

| TTC | AGT | CCC | GTG | CCC | AGT | TCC | ACC | TTC | ACC | TCC | AGC | TCC | ACC | TAT | ACC | 1155 |
| Phe | Ser | Pro | Val | Pro | Ser | Ser | Thr | Phe | Thr | Ser | Ser | Ser | Thr | Tyr | Thr |     |
| 265 |     |     |     |     | 270 |     |     |     |     | 275 |     |     |     |     |     |     |

| CCC | GGT | GAC | TGT | CCC | AAC | TTT | GCG | GCT | CCC | CGC | AGA | GAG | GTG | GCA | CCA | 1203 |
| Pro | Gly | Asp | Cys | Pro | Asn | Phe | Ala | Ala | Pro | Arg | Arg | Glu | Val | Ala | Pro |     |
| 280 |     |     |     |     | 285 |     |     |     |     | 290 |     |     |     |     | 295 |     |

| CCC | TAT | CAG | GGG | GCT | GAC | CCC | ATC | CTT | GCG | ACA | GCC | CTC | GCC | TCC | GAC | 1251 |

```
Pro  Tyr  Gln  Gly  Ala  Asp  Pro  Ile  Leu  Ala  Thr  Ala  Leu  Ala  Ser  Asp
               300                      305                      310

CCC  ATC  CCC  AAC  CCC  CTT  CAG  AAG  TGG  GAG  GAC  AGC  GCC  CAC  AAG  CCA              1299
Pro  Ile  Pro  Asn  Pro  Leu  Gln  Lys  Trp  Glu  Asp  Ser  Ala  His  Lys  Pro
               315                      320                      325

CAG  AGC  CTA  GAC  ACT  GAT  GAC  CCC  GCG  ACG  CTG  TAC  GCC  GTG  GTG  GAG              1347
Gln  Ser  Leu  Asp  Thr  Asp  Asp  Pro  Ala  Thr  Leu  Tyr  Ala  Val  Val  Glu
               330                      335                      340

AAC  GTG  CCC  CCG  TTG  CGC  TGG  AAG  GAA  TTC  GTG  CGG  CGC  CTA  GGG  CTG              1395
Asn  Val  Pro  Pro  Leu  Arg  Trp  Lys  Glu  Phe  Val  Arg  Arg  Leu  Gly  Leu
               345                      350                      355

AGC  GAC  CAC  GAG  ATC  GAT  CGG  CTG  GAG  CTG  CAG  AAC  GGG  CGC  TGC  CTG              1443
Ser  Asp  His  Glu  Ile  Asp  Arg  Leu  Glu  Leu  Gln  Asn  Gly  Arg  Cys  Leu
360                     365                      370                      375

CGC  GAG  GCG  CAA  TAC  AGC  ATG  CTG  GCG  ACC  TGG  AGG  CGG  CGC  ACG  CCG              1491
Arg  Glu  Ala  Gln  Tyr  Ser  Met  Leu  Ala  Thr  Trp  Arg  Arg  Arg  Thr  Pro
               380                      385                      390

CGG  CGC  GAG  GCC  ACG  CTG  GAG  CTG  CTG  GGA  CGC  GTG  CTC  CGC  GAC  ATG              1539
Arg  Arg  Glu  Ala  Thr  Leu  Glu  Leu  Leu  Gly  Arg  Val  Leu  Arg  Asp  Met
               395                      400                      405

GAC  CTG  CTG  GGC  TGC  CTG  GAG  GAC  ATC  GAG  GAG  GCG  CTT  TGC  GGC  CCC              1587
Asp  Leu  Leu  Gly  Cys  Leu  Glu  Asp  Ile  Glu  Glu  Ala  Leu  Cys  Gly  Pro
               410                      415                      420

GCC  GCC  CTC  CCG  CCC  GCG  CCC  AGT  CTT  CTC  AGA  TGAGGCTGCG  CCCTGCGGGC              1640
Ala  Ala  Leu  Pro  Pro  Ala  Pro  Ser  Leu  Leu  Arg
               425                      430

AGCTCTAAGG  ACCGTCCTGC  GAGATCGCCT  TCCAACCCCA  CTTTTTTCTG  GAAAGGAGGG              1700

GTCCTGCAGG  GGCAAGCAGG  AGCTAGCAGC  CGCCTACTTG  GTGCTAACCC  CTCGATGTAC              1760

ATAGCTTTTC  TCAGCTGCCT  GCGCGCCGCC  GACAGTCAGC  GCTGTGCGCG  CGGAGAGAGG              1820

TGCGCCGTGG  GCTCAAGAGC  CTGAGTGGGT  GGTTTGCGAG  GATGAGGGAC  GCTATGCCTC              1880

ATGCCCGTTT  TGGGTGTCCT  CACCAGCAAG  GCTGCTCGGG  GGCCCCTGGT  TCGTCCCTGA              1940

GCCTTTTTCA  CAGTGCATAA  GCAGTTTTTT  TTGTTTTTGT  TTTGTTTTGT  TTTGTTTTA              2000

AATCAATCAT  GTTACACTAA  TAGAAACTTG  GCACTCCTGT  GCCCTCTGCC  TGGACAAGCA              2060

CATAGCAAGC  TGAACTGTCC  TAAGGCAGGG  GCGAGCACGG  AACAATGGGG  CCTTCAGCTG              2120

GAGCTGTGGA  CTTTTGTACA  TACACTAAAA  TTCTGAAGTT  AAAAAAAAAA  AAAAA              2175
```

(2) INFORMATION FOR SEQ ID NO:2:

(i) SEQUENCE CHARACTERISTICS:
        (A) LENGTH: 455 amino acids
        (B) TYPE: amino acid
        (D) TOPOLOGY: linear (ii) MOLECULE TYPE: protein (xi) SEQUENCE DESCRIPTION: SEQ ID NO:2:

```
Met  Gly  Leu  Ser  Thr  Val  Pro  Asp  Leu  Leu  Leu  Pro  Leu  Val  Leu  Leu
-21  -20                 -15                      -10

Glu  Leu  Leu  Val  Gly  Ile  Tyr  Pro  Ser  Gly  Val  Ile  Gly  Leu  Val  Pro
     -5                     1                     5                       10

His  Leu  Gly  Asp  Arg  Glu  Lys  Arg  Asp  Ser  Val  Cys  Pro  Gln  Gly  Lys
                15                      20                      25

Tyr  Ile  His  Pro  Gln  Asn  Asn  Ser  Ile  Cys  Cys  Thr  Lys  Cys  His  Lys
               30                      35                      40

Gly  Thr  Tyr  Leu  Tyr  Asn  Asp  Cys  Pro  Gly  Pro  Gly  Gln  Asp  Thr  Asp
          45                      50                      55
```

| | | | | | | | | | | | | | | |
|---|---|---|---|---|---|---|---|---|---|---|---|---|---|---|
| Cys | Arg | Glu | Cys | Glu | Ser | Gly | Ser | Phe | Thr | Ala | Ser | Glu | Asn | His | Leu |
| 60 | | | | 65 | | | | | 70 | | | | | 75 |
| Arg | His | Cys | Leu | Ser | Cys | Ser | Lys | Cys | Arg | Lys | Glu | Met | Gly | Gln | Val |
| | | | 80 | | | | 85 | | | | | | 90 | |
| Glu | Ile | Ser | Ser | Cys | Thr | Val | Asp | Arg | Asp | Thr | Val | Cys | Gly | Cys | Arg |
| | | | 95 | | | | 100 | | | | | 105 | | |
| Lys | Asn | Gln | Tyr | Arg | His | Tyr | Trp | Ser | Glu | Asn | Leu | Phe | Gln | Cys | Phe |
| | | 110 | | | | | 115 | | | | | 120 | | |
| Asn | Cys | Ser | Leu | Cys | Leu | Asn | Gly | Thr | Val | His | Leu | Ser | Cys | Gln | Glu |
| | 125 | | | | | 130 | | | | 135 | | | | |
| Lys | Gln | Asn | Thr | Val | Cys | Thr | Cys | His | Ala | Gly | Phe | Phe | Leu | Arg | Glu |
| 140 | | | | 145 | | | | | 150 | | | | | 155 |
| Asn | Glu | Cys | Val | Ser | Cys | Ser | Asn | Cys | Lys | Lys | Ser | Leu | Glu | Cys | Thr |
| | | | 160 | | | | 165 | | | | | 170 | | |
| Lys | Leu | Cys | Leu | Pro | Gln | Ile | Glu | Asn | Val | Lys | Gly | Thr | Glu | Asp | Ser |
| | | 175 | | | | | 180 | | | | | 185 | | |
| Gly | Thr | Thr | Val | Leu | Leu | Pro | Leu | Val | Ile | Phe | Phe | Gly | Leu | Cys | Leu |
| | | 190 | | | | 195 | | | | | 200 | | | |
| Leu | Ser | Leu | Leu | Phe | Ile | Gly | Leu | Met | Tyr | Arg | Tyr | Gln | Arg | Trp | Lys |
| | 205 | | | | 210 | | | | | 215 | | | | |
| Ser | Lys | Leu | Tyr | Ser | Ile | Val | Cys | Gly | Lys | Ser | Thr | Pro | Glu | Lys | Glu |
| 220 | | | | 225 | | | | | 230 | | | | | 235 |
| Gly | Glu | Leu | Glu | Gly | Thr | Thr | Thr | Lys | Pro | Leu | Ala | Pro | Asn | Pro | Ser |
| | | | 240 | | | | 245 | | | | | 250 | | |
| Phe | Ser | Pro | Thr | Pro | Gly | Phe | Thr | Pro | Thr | Leu | Gly | Phe | Ser | Pro | Val |
| | | 255 | | | | | 260 | | | | | 265 | | |
| Pro | Ser | Ser | Thr | Phe | Thr | Ser | Ser | Thr | Tyr | Thr | Pro | Gly | Asp | Cys |
| | 270 | | | | 275 | | | | | 280 | | | | |
| Pro | Asn | Phe | Ala | Ala | Pro | Arg | Arg | Glu | Val | Ala | Pro | Pro | Tyr | Gln | Gly |
| | 285 | | | | 290 | | | | | 295 | | | | |
| Ala | Asp | Pro | Ile | Leu | Ala | Thr | Ala | Leu | Ala | Ser | Asp | Pro | Ile | Pro | Asn |
| 300 | | | | 305 | | | | 310 | | | | | 315 | |
| Pro | Leu | Gln | Lys | Trp | Glu | Asp | Ser | Ala | His | Lys | Pro | Gln | Ser | Leu | Asp |
| | | | 320 | | | | | 325 | | | | | 330 | |
| Thr | Asp | Asp | Pro | Ala | Thr | Leu | Tyr | Ala | Val | Val | Glu | Asn | Val | Pro | Pro |
| | | 335 | | | | | 340 | | | | | 345 | | |
| Leu | Arg | Trp | Lys | Glu | Phe | Val | Arg | Arg | Leu | Gly | Leu | Ser | Asp | His | Glu |
| | | 350 | | | | | 355 | | | | 360 | | | |
| Ile | Asp | Arg | Leu | Glu | Leu | Gln | Asn | Gly | Arg | Cys | Leu | Arg | Glu | Ala | Gln |
| | 365 | | | | 370 | | | | | 375 | | | | |
| Tyr | Ser | Met | Leu | Ala | Thr | Trp | Arg | Arg | Arg | Thr | Pro | Arg | Arg | Glu | Ala |
| 380 | | | | 385 | | | | | 390 | | | | | 395 |
| Thr | Leu | Glu | Leu | Leu | Gly | Arg | Val | Leu | Arg | Asp | Met | Asp | Leu | Leu | Gly |
| | | | 400 | | | | 405 | | | | | 410 | | |
| Cys | Leu | Glu | Asp | Ile | Glu | Glu | Ala | Leu | Cys | Gly | Pro | Ala | Ala | Leu | Pro |
| | | 415 | | | | 420 | | | | 425 | | | | |
| Pro | Ala | Pro | Ser | Leu | Leu | Arg |
| | | 430 | | | | |

( 2 ) INFORMATION FOR SEQ ID NO:3:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( i i ) MOLECULE TYPE: protein ( x i ) SEQUENCE DESCRIPTION: SEQ ID NO:3:

GGNGTYCCNT TYATRTARGT DGGNGT                26

( 2 ) INFORMATION FOR SEQ ID NO:4:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:4:

GGNGTYCCNT TYATRTA                17

( 2 ) INFORMATION FOR SEQ ID NO:5:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:5:

TTYATRTARG TDGGNGT                17

( 2 ) INFORMATION FOR SEQ ID NO:6:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:6:

CGGCCGATGG GCCTCTCCAC CGTGCCT                27

( 2 ) INFORMATION FOR SEQ ID NO:7:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:7:

AATAGTATTT CTAATCTGGG GTAGGCA                27

( 2 ) INFORMATION FOR SEQ ID NO:8:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:8:

Met Asp Ser Val Cys Pro
1               5

(2) INFORMATION FOR SEQ ID NO:9:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:9:

AATTCATGGA TAGTGTGTGT CCC          23

(2) INFORMATION FOR SEQ ID NO:10:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:10:

GTACCTATCA CACACAGGGG TTC          23

(2) INFORMATION FOR SEQ ID NO:11:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:11:

Ala Gln Val Ala Phe Thr Pro Tyr Ala Pro Glu Pro Gly Ser Thr Cys
1               5                   10                  15

Arg Leu Arg Glu Tyr Tyr
                20

(2) INFORMATION FOR SEQ ID NO:12:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: cDNA (xi) SEQUENCE DESCRIPTION: SEQ ID NO:12:

Leu Cys Ala Pro Leu Arg Lys
1               5

(2) INFORMATION FOR SEQ ID NO:13:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:13:

```
Cys Arg Pro Gly Phe Gly Val Ala Arg
1               5
```

( 2 ) INFORMATION FOR SEQ ID NO:14:

( i ) SEQUENCE CHARACTERISTICS:
        ( A ) LENGTH: 11 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:14:

```
Glu Tyr Tyr Asp Gln Thr Ala Gln Met Cys Cys
1               5                   10
```

( 2 ) INFORMATION FOR SEQ ID NO:15:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:15:

```
Glu Tyr Tyr Asp Gln Thr Ala Gln Met Cys Cys Ser
1               5                   10
```

( 2 ) INFORMATION FOR SEQ ID NO:16:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:16:

```
Ser Cys Gly Pro Ser Tyr Pro Asp
1               5
```

( 2 ) INFORMATION FOR SEQ ID NO:17:

( i ) SEQUENCE CHARACTERISTICS:
        ( A ) LENGTH: 13 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:17:

```
Phe Thr Pro Tyr Ala Pro Glu Pro Gly Ser Thr Cys Arg
1               5                   10
```

( 2 ) INFORMATION FOR SEQ ID NO:18:

( i ) SEQUENCE CHARACTERISTICS:
        ( A ) LENGTH: 13 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:18:

```
Leu  Arg  Glu  Tyr  Tyr  Asp  Gln  Thr  Ala  Gln  Met  Cys  Cys
1                 5                             10
```

( 2 ) INFORMATION FOR SEQ ID NO:19:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:19:

```
Pro  Gly  Trp  Tyr  Cys  Ala  Leu  Ser  Lys
1                 5
```

( 2 ) INFORMATION FOR SEQ ID NO:20:

( i ) SEQUENCE CHARACTERISTICS:
        ( A ) LENGTH: 17 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:20:

```
Ala  Gln  Val  Ala  Phe  Thr  Pro  Tyr  Ala  Pro  Glu  Pro  Gly  Ser  Thr  Cys
1                 5                             10                            15

Arg
```

( 2 ) INFORMATION FOR SEQ ID NO:21:

( i ) SEQUENCE CHARACTERISTICS:
        ( A ) LENGTH: 15 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:21:

```
Val  Ala  Phe  Thr  Pro  Tyr  Ala  Pro  Glu  Pro  Gly  Ser  Thr  Cys  Arg
1                 5                             10                      15
```

( 2 ) INFORMATION FOR SEQ ID NO:22:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:22:

```
Cys  Arg  Pro  Gly  Phe  Gly  Val  Ala  Arg
1                 5
```

( 2 ) INFORMATION FOR SEQ ID NO:23:

( i ) SEQUENCE CHARACTERISTICS:
        ( A ) LENGTH: 13 amino acids
        ( B ) TYPE: amino acid
        ( C ) STRANDEDNESS: single
        ( D ) TOPOLOGY: linear ( i i ) MOLECULE TYPE: peptide (x i) SEQUENCE DESCRIPTION: SEQ ID NO:23:

Ile Cys Thr Cys Arg Pro Gly Trp Tyr Cys Ala Leu Ser
1               5                   10

(2) INFORMATION FOR SEQ ID NO:24:

(i) SEQUENCE CHARACTERISTICS:
        (A) LENGTH: 20 amino acids
        (B) TYPE: amino acid
        (C) STRANDEDNESS: single
        (D) TOPOLOGY: linear (i i) MOLECULE TYPE: peptide (x i) SEQUENCE DESCRIPTION: SEQ ID NO:24:

Pro Gly Thr Glu Thr Ser Asp Val Val Cys Lys Pro Cys Ala Pro Gly
1               5                   10                  15

Thr Phe Ser Lys
            20

(2) INFORMATION FOR SEQ ID NO:25:

(i) SEQUENCE CHARACTERISTICS:
        (A) LENGTH: 20 amino acids
        (B) TYPE: amino acid
        (C) STRANDEDNESS: single
        (D) TOPOLOGY: linear (i i) MOLECULE TYPE: peptide (x i) SEQUENCE DESCRIPTION: SEQ ID NO:25:

Cys Arg Pro Gly Phe Gly Val Ala Arg Pro Gly Thr Glu Thr Ser Asp
1               5                   10                  15

Val Val Cys Lys
            20

(2) INFORMATION FOR SEQ ID NO:26:

(i) SEQUENCE CHARACTERISTICS:
        (A) LENGTH: 18 amino acids
        (B) TYPE: amino acid
        (C) STRANDEDNESS: single
        (D) TOPOLOGY: linear (i i) MOLECULE TYPE: peptide (x i) SEQUENCE DESCRIPTION: SEQ ID NO:26:

Thr Ser Asp Thr Val Cys Asp Ser Cys Glu Asp Ser Thr Tyr Thr Gln
1               5                   10                  15

Leu Trp